US011008623B2

(12) United States Patent
Pu

(10) Patent No.: US 11,008,623 B2
(45) Date of Patent: May 18, 2021

(54) COMPARING PIGN TRANSCRIPTION AND TRANSLATION LEVELS AND SEQUENCING TO LOCATE A PIGN MUTATION

(71) Applicant: The Penn State Research Foundation, University Park, PA (US)

(72) Inventor: Jeffrey Pu, Hummelstown, PA (US)

(73) Assignee: THE PENN STATE RESEARCH FOUNDATION, University Park, PA (US)

( * ) Notice: Subject to any disclaimer, the term of this patent is extended or adjusted under 35 U.S.C. 154(b) by 993 days.

(21) Appl. No.: 15/434,774

(22) Filed: Feb. 16, 2017

(65) Prior Publication Data

US 2017/0233819 A1    Aug. 17, 2017

Related U.S. Application Data

(60) Provisional application No. 62/296,345, filed on Feb. 17, 2016, provisional application No. 62/418,422, filed on Nov. 7, 2016.

(51) Int. Cl.
*C12Q 1/6886* (2018.01)

(52) U.S. Cl.
CPC ...... *C12Q 1/6886* (2013.01); *C12Q 2600/112* (2013.01); *C12Q 2600/158* (2013.01)

(58) Field of Classification Search
None
See application file for complete search history.

(56) References Cited

U.S. PATENT DOCUMENTS

| 2012/0157329 A1 | 6/2012 | Giraldo-Castellano et al. |
| 2013/0274127 A1 | 10/2013 | Baker et al. |
| 2014/0315212 A1 | 10/2014 | Pierce et al. |

OTHER PUBLICATIONS

Allegro, Alessandro, et al. "Circulating microRNAs: new biomarkers in diagnosis, prognosis and treatment of cancer." International journal of oncology 41.6 (2012): 1897-1912.*
American Society of Hematology, webpage (https://www.hematology.org/education/patients/blood-cancers), 1 page, downloaded Jul. 27, 2020.*
Jennings, C. Darrell, and Kenneth A. Foon. "Recent advances in flow cytometry: application to the diagnosis of hematologic malignancy." Blood, The Journal of the American Society of Hematology 90.8 (1997): 2863-2892.*
Blalock, William L., et al. "A role for PKR in hematologic malignancies." Journal of cellular physiology 223.3 (2010): 572-591.*
Craig, Fiona E., and Kenneth A. Foon. "Flow cytometric immunophenotyping for hematologic neoplasms." Blood 111.8 (2008): 3941-3967.*
Teye, Emmanuel K., et al. "PIGN gene expression aberration is associated with genomic instability and leukemic progression in acute myeloid leukemia with myelodysplastic features." Oncotarget 8.18 (2017): 29887.*
Byrne et al., 2014 "Progressive Genomic Instability in the Nup98-HoxD13 Model of MDS Correlates with Loss of the PIG—A Gene Product", Neoplasia, vol. 16, No. 8, pp. 327-633.
Carter et al., 2006 "A signature of chromosomal instability inferred from gene expression profiles predicts clinical outcome in multiple human cancers", Nature Genetics, vol. 38, No. 9, pp. 1043-1048.
Chen et al., 2001 "Glycophosphatidylinositol-anchored Protein Deficiency as a Marker of Mutator Phenotypes in Cancer1", Cancer Research, vol. 61, pp. 654-658.
Gonorazky et al., 2016 "RNAseq analysis for the diagnosis of muscular dystrophy", Annals of Clinical and Translational Neurology, vol. 3, No. 1, pp. 55-60.
Hasanali et al., 2015 "Epigenetic therapy overcomes treatment resistance in T-cell prolymphocytic leukemia", Sci Transl Med., vol. 7, No. 293, pp. 1-24.
Hong et al., 1999 "Pig-n, a Mammalian Homologue of Yeast Mcd4p, Is Involved in Transferring Phosphoethanolamine to the First Mannose of the Glycosylphosphatidylinositol", The Journal of Biological Chemistry, vol. 274, No. 49, pp. 35099-35106.
Niblock et al., 2016 "Retention of hexanucleotide repeat-containing intron in C9orf72 mRNA: implications for the pathogenesis of ALS/FTD", Acta Neuropathologica Communications, vol. 4, No. 18, pp. 1-12.
Ohba et al., 2014 "PIGN mutations cause congenital anomalies, developmental delay, hypotonia, epilepsy, and progressive cerebellar atrophy", Neurogenetics, vol. 15, pp. 85-92.
Ostgard et al., 2010 "Reasons for treating secondary AML as de novo AML", European Journal of Haematology, vol. 85, pp. 217-226.
Parks et al., 1998 "An ACTH-producing small cell lung cancer expresses aberrant glucocorticoid receptor transcripts from a normal gene", Molecular and Cellular Endocrinology, vol. 142, pp. 175-181.
Pellagatti et al., 2006, "Gene expression profiles of CD34+ cells in myelodysplastic syndromes: involvement of interferon-stimulated genes and correlation to FAB subtype and karyotype", Blood, vol. 108, No. 1, pp. 337-345.
Peruzzi et al., 2010 "The use of PIG—A as a sentinel gene for the study of the somatic mutation rate and of mutagenic agents in vivo", Mutation Research, vol. 705, pp. 3-10.
Pu et al., 2012 "The small population of PIG—A mutant cells in myelodysplastic syndromes do not arise from multipotent hematopoietic stem cells", Haematologica, vol. 97, No. 8, pp. 1225-1233.
Pu et al., 2013 "The origin of GPI-AP deficient cells in MDS, MPD, and aplastic anemia and its signifiance in predicting leukemic transformation", Journal of Clinical Oncology, Abstract, pp. 1-2.

(Continued)

*Primary Examiner* — G Steven Vanni
(74) *Attorney, Agent, or Firm* — Troutman Pepper Hamilton Sanders LLP; Christopher C. Close, Jr.

(57) ABSTRACT

The invention provides a method for determining the level of risk for development or progression of a hematologic neoplasia in a subject by analyzing the level of a phosphatidylinositol glycan anchor biosynthesis protein, and providing an appropriate treatment or preventive measure, on the basis of this risk.

5 Claims, 18 Drawing Sheets
(8 of 18 Drawing Sheet(s) Filed in Color)
Specification includes a Sequence Listing.

(56) References Cited

OTHER PUBLICATIONS

Puddu et al., 2015 "Synthetic viability genomic screening defines Sae2 function in DNA repair", The EMBO Journal, vol. 34, pp. 1509-1522.

Sanjana et al., 2014 "Improved vectors and genome-wide libraries for CRISPR screening", Nat Methods., vol. 11, No. 8:783-784, pp. 1-5.

Sheffer et al., 2009 "Association of survival and disease progression with chromosomal instability: A genomic exploration of colorectal cancer", PNAS, vol. 106, No. 17, pp. 7131-7136.

Tohyama etal., 1994 "Establishment and characterization of a novel myeloid cell line from the bone marrow of a patient with the myelodysplastic syndrome", British Journal of Haematology, vol. 87, pp. 235-242.

Trapnell et al., 2009 "TopHat: discovering splice junctions with RNA-Seq", Bioinformatics, vol. 25, No. 9, pp. 1105-1111.

Turinetto et al., 2015 "Survey and Summary: Multiple facets of histone variant H2AX: a DNA double-strand-break marker with several biological functions", Nucleic Acids Research, vol. 43, No. 5, pp. 2489-2498.

Yada et al., 2001 "Its8, a Fission Yeast Homolog of Mcd4 and Pig-n, Is Involved in GPI Anchor Synthesis and Shares an Essential Function with Calcineurin in Cytokinesis", The Journal of Biological Chemistry, vol. 276, No. 17, April Issue, pp. 13579-13586.

Burrell et al., 2013 "Replication stress links structural and numerical cancer chromosomal instability", Nature, vol. 494, pp. 492-499.

Araten et al., 2010 "A quantitative analysis of genomic instability in lymphoid and plasma cell neoplasms based on the PIG—A gene", Mutation Research, vol. 686(1-2), pp. 1-16.

Araten et al., 2005 "A Quantitative Measurement of the Human Somatic Mutation Rate", Cancer Research, vol. 65: (18), pp. 8111-8117.

Altschul et al., 1990 "Basic Local Alignment Search Tool", J. Mol. Biol., vol. 215, pp. 403-410.

* cited by examiner

| Position[a] | Exon | Nucleotide change | Type | AA Change | SIFT[b] |
|---|---|---|---|---|---|
| 11,031 | 2 | G>A | Non-synonymous | p.S9N | neutral |
| 11,470 | 4 | C>G | Non-synonymous | p.P80R | neutral |
| 12,379 | 5 | C>- | Frameshift deletion | p.N131fs | NA |

[a] Position in GenBank NC_000017.9
[b] http://p53.iarc.fr/TP53GeneVariations.aspx

Figure 6

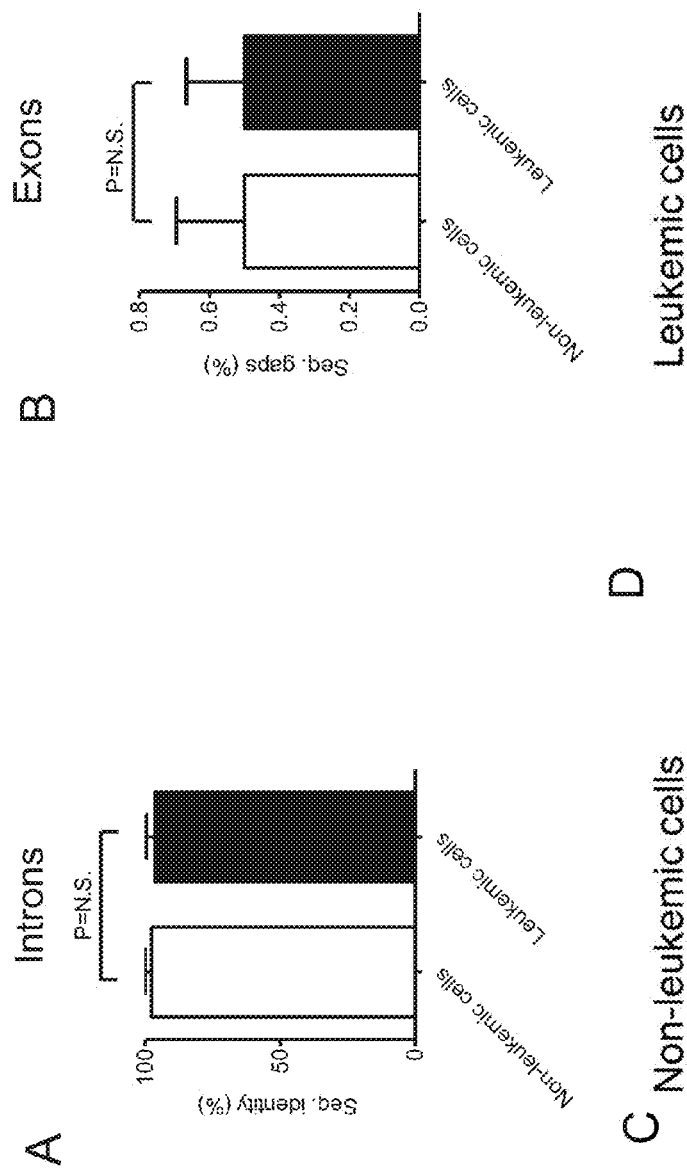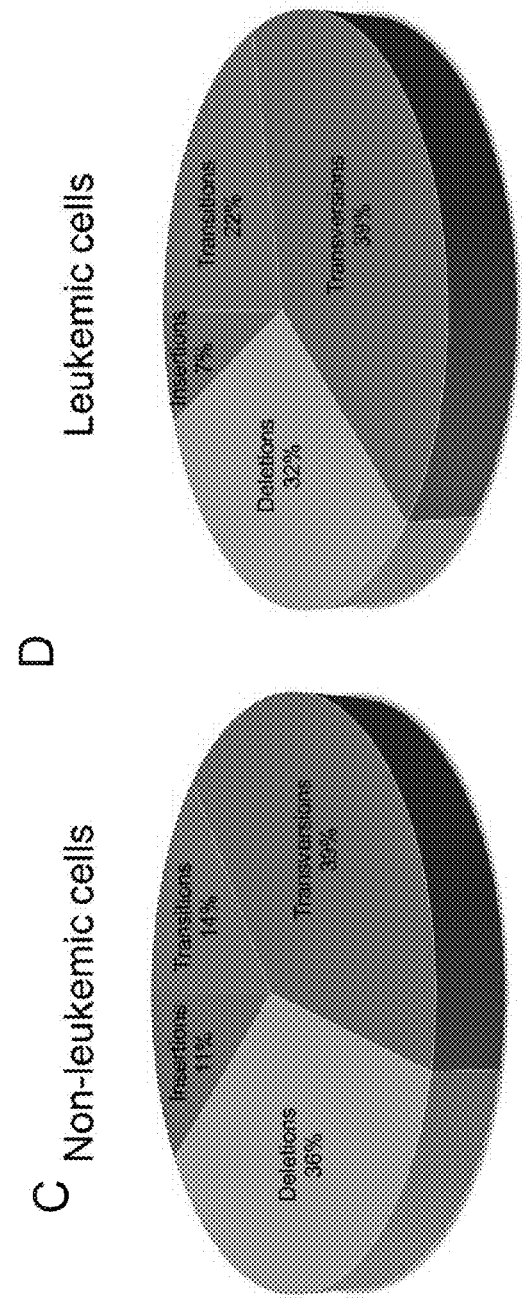
Figures 7A-Figure 7D

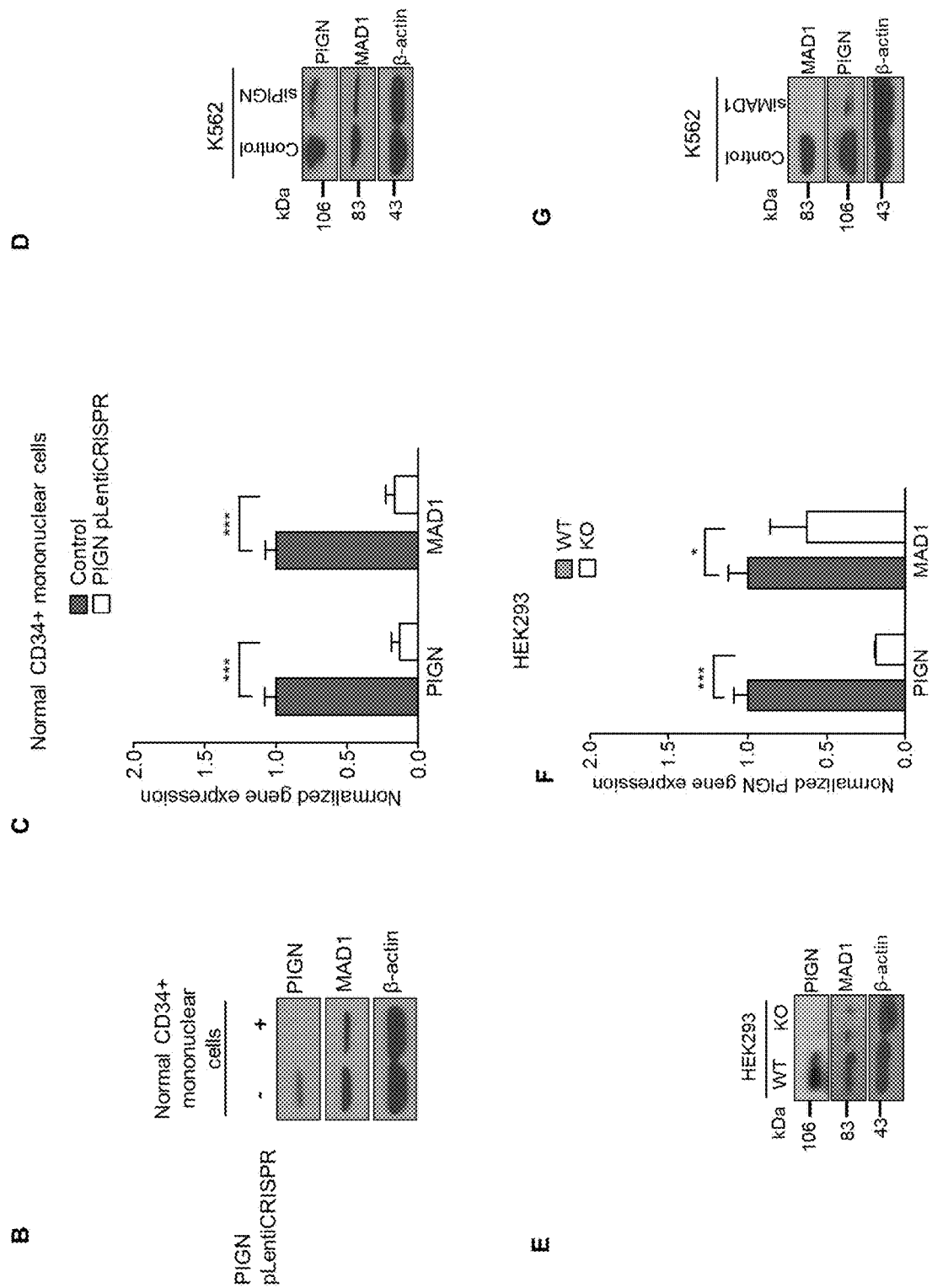

SEQUENCE LISTING

<160> NUMBER OF SEQ ID NOS: 1

<210> SEQ ID NO 1
<211> LENGTH: 24
<212> TYPE: DNA
<213> ORGANISM: Artificial Sequence
<220> FEATURE:
<223> OTHER INFORMATION: gRNA to PIGN at exon 4

```
<400> SEQUENCE: 1
aaacggtcat gtagctctga tagc                                              24
```

US 11,008,623 B2

COMPARING PIGN TRANSCRIPTION AND TRANSLATION LEVELS AND SEQUENCING TO LOCATE A PIGN MUTATION

CROSS REFERENCE TO RELATED APPLICATIONS

This application claims priority to U.S. Provisional Application No. 62/296,345, filed Feb. 17, 2016 and U.S. Provisional Application No. 62/418,422, filed Nov. 7, 2016 which are hereby incorporated by reference herein in their entirety.

BACKGROUND OF THE INVENTION

Myelodysplastic syndromes (MDS) are a heterogeneous collection of clonal hematological malignancies that affect about 13,000 people annually in the United States alone with about a one-third propensity of progression into acute myeloid leukemia (AML) (American Cancer Society. Cancer Facts & FIGS. 2016). MDS is conventionally classified as AML with myelodysplasia-related changes (AML-MRC) when blood or bone marrow blast populations reach or exceed 20% with dysplastic morphology in 50% or more cells in more than two myeloid lineages (Arber et al., Blood. 2016, 27:2391-2405; Vardiman and Reichard, Am. J. Clin. Pathol. 2015, 144:29-43). AML is more aggressive and molecularly diverse and involves unconstrained proliferation of aberrant myeloid progenitor cells. These aberrant myeloid progenitor cells possess genetic aberrations, populate the bone marrow and peripheral blood, and contribute to leukemia progression by driving clonal evolution (Genovese et al., N. Engl. J. Med. 2014, 371:2477-2487).

Approximately in 50% of AML the aberrant myeloid progenitor cells possess clonal chromosomal instability (CIN) (Grove et al., Disease Models & Mechanisms, 2014, 7:941-951; Seifert et al., Leukemia, 2009, 23:656-663). AML may develop de novo or secondary to the treatment of other cancers with chemotherapy or radiotherapy; or may evolve from other bone marrow failure conditions such as myelodysplastic syndromes (MDS), aplastic anemia, or myeloproliferative neoplasms (Ostgard et al., European Journal of Haematology, 2010, 85:217-226). It has been observed that high frequency of genomic instability is frequently associated with cancer initiation and progression (Rabinovitch el al, Laboratory Investigation, 1989, 60:65-71; Tainsky et al., Cancer Metastasis Reviews, 1995, 14:43-48; Donehower et al, Progress in Clinical and Biological Research, 1996, 395:1-11; Sheffer et al., PNAS, 2009, 106:7131-7136). In fact, genomic instability is responsible for the clonal accumulation of genetic aberrations that contribute to AML transformation and progression; and has been indicated as a driver of the clonal evolution of MDS to AML (Byrne et al., Neoplasia, 2014, 16:627-633). Therefore, there is a need in the art for reliable markers of hematological neoplasia which can be used as prognostic indicators for development of hematological neoplasia and advancement of MDS to AML.

SUMMARY OF THE INVENTION

In one embodiment, the invention relates to a method for treating or preventing a hematological neoplasia in a subject, the method comprising the steps of determining the level of at least one biomarker in a sample of the subject, comparing the level of the biomarker in the sample of the subject with a comparator control, diagnosing the subject as having increased risk for development or progression of a hematological neoplasia when the level of the biomarker in the sample of the subject is increased or reduced at a statistically significant amount when compared with the level of the biomarker of the comparator control, and providing or recommending a course of treatment based on the diagnosis.

In one embodiment, the hematological neoplasia is one or more of acute myeloblastic leukemia (AML), acute lymphoblastic leukemia (ALL), myelodysplastic syndrome (MDS), chronic myeloid leukemia (CIVIL), lymphoproliferative disorders (LPD), chronic lymphocytic leukemia (CLL), hodgkin's lymphoma, and non-hodgkin's lymphomas.

In one embodiment, the sample is a biological sample from a human.

In one embodiment, the level of the biomarker in the sample is determined by measuring one or more of: the level of at least one mutated phosphatidylinositol glycan anchor biosynthesis protein in the sample, wherein an increased amount of at least one mutated phosphatidylinositol glycan anchor biosynthesis protein as compared to a comparator control is a prognostic indicator of a hematological neoplasia; the level of at least one wild-type phosphatidylinositol glycan anchor biosynthesis protein in the sample, wherein a decreased amount of at least one full length or wild-type phosphatidylinositol glycan anchor biosynthesis protein as compared to a comparator control is a prognostic indicator of a hematological neoplasia; the level of at least one nucleic acid encoding a mutated phosphatidylinositol glycan anchor biosynthesis protein in the sample, wherein an increased amount of at least one nucleic acid encoding a mutated phosphatidylinositol glycan anchor biosynthesis protein as compared to a comparator control is a prognostic indicator of a hematological neoplasia; and the frequency of at least one glycophosphatidylinositol-anchored proteins (GPI-AP) in the sample, wherein a decreased amount of at least one GPI-AP proteins as compared to a comparator control is a prognostic indicator of a hematological neoplasia.

In one embodiment, the phosphatidylinositol glycan anchor biosynthesis protein is one or more of PIGA, PIGH, PIGF, PIGC, PIGQ, PIGL, PIGB, PIGW, PIGX, PIGU, PIGT, PIGO, PIGN, PIGM, PIGS, PIGV, PIGZ, PIGG, PIGY, and PIGK.

In one embodiment, the GPI-AP is one or more of 1G7, 5'-nucleotidase, acetylcholinesterase, alkaline phosphatase, CAPRIN1, CD14, CD16, CD16b, CD52, CD55, CD59, CEA, dipeptidase, folate-binding protein, FOLR1, LFA-3, NCAM, PH-20, procyclin, Qa-2, scrapie prion protein, Thy-1, and VSG.

In one embodiment, the comparator control is one or more of a positive control, a negative control, a historical control, a historical norm, and the level of a reference molecule in the biological sample.

In one embodiment, the method further comprises combining the diagnosis with a prognostic scoring system to provide or recommend a course of treatment to a patient.

In one embodiment, the course of treatment is one or more of a gene therapy, a drug, a clinical trial, a referral to a specialist, counseling, and monitoring the subject for one or more of development and advancement of a hematological neoplasia.

In one embodiment, the course of treatment comprises providing a modulator of one or more of PIGN, MAD1 and PKR to a patient. In one embodiment, the modulator of PIGN comprises an activator of PIGN or an inhibitor of a negative regulator of PIGN. In one embodiment, the modulator of MAD1 comprises an activator of MAD1 or an inhibitor of MAX. In one embodiment, the modulator of PKR comprises an inhibitor of PKR.

In one embodiment, the invention relates to a therapeutic composition comprising a modulator of PIGN. In one embodiment, the modulator of PIGN comprises an activator of PIGN or an inhibitor of a negative regulator of PIGN.

In one embodiment, the invention relates to a method for treating or preventing cancer in a subject comprising administering to a subject an effective amount of a therapeutic composition comprising a modulator of PIGN. In one embodiment, the modulator increases one or more of transcription, translation, and activity of PIGN. In one embodiment, the modulator decreases one or more of transcription, translation, and activity of a negative regulator of PIGN. In one embodiment, the modulator is one or more of a nucleic acid, a protein, a peptide, a peptidomimetic, a chemical compound and a small molecule. In one embodiment, the cancer is acute myeloid leukemia.

BRIEF DESCRIPTION OF THE DRAWINGS

The patent or application file contains at least one drawing executed in color. Copies of this patent or patent application publication with color drawing(s) will be provided by the Office upon request and payment of the appropriate fee.

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 2A depicts that RT-qPCR analysis of PIGN in patient samples showed a subgroup of MDS/AML-MRC patients had a significant difference (***$p<0.0001$) in PIGN gene expression than normal controls. FIG. 2B depicts that PIGN protein expression was lost or suppressed in the same subpopulation of patients who had increased copies of the PIGN transcript. FIG. 2C depicts sequence analyses on CD34+ cells revealed the presence of intron fragment retentions resulting from splice defects between exons 14 and 15 caused frameshifts and premature termination; samples M1, M2 and M4 were from AML patients; samples 1-11 represented the results of RNA-seq junction file data analyses from AML patients in the dbGAP study phs001027.v1.p1. Intron base positions (bp) were based on NCBI reference sequence NG_033144.1.

FIG. 3, comprising FIG. 3A depicts RT-qPCR data demonstrating that PIGN gene expression in leukemic cells from AML patients M1 and M2 were significantly (***$p<0.0001$) higher (i.e. 3- to 7-fold) than in normal control cells from healthy individual (NL). One way ANOVA Tukey's post-hoc test; error bars represent standard deviation from the mean fold change in gene expression. FIG. 3B depicts a western blot showing that PIGN protein expression was lost in patients M1 and M2. FIG. 3C depicts experimental results demonstrating that the frequency of GPI-AP loss was much higher in leukemic clones than in the non-leukemic clones in the respective AML patients. Leukemic and non-leukemic cells were sorted using the following markers HLA-DR, CD13, CD117 and CD45.

FIG. 4, comprising FIG. 4A depicts a western blot showing that the PIGN protein was progressively lost in an AML patient (M4 and M5). FIG. 4B depicts quantification of PIGN gene expression showing that expression was significantly (*$p<0.0001$) downregulated from pre-treatment (M4) to relapse (M5). Error bars represent standard deviation from the mean fold change in gene expression. FIG. 4C and FIG. 4D depict analysis of PIGN expression in MDS92 and MDS-L, which shared the same origin. FIG. 4C depicts a western blot showing that PIGN protein was progressively lost from the MDS phase (MDS92 cells) to the leukemic phase (MDS-L cells) and FIG. 4D depicts PIGN gene expression was significantly (*$p<0.0001$) higher in MDS92 cells than in MDS-L cells. FIG. 4E depicts experimental results demonstrating that PIGN protein expression was more suppressed in the myeloblastic phase (KG1) comparing to its myeloid derivative (KG1a). FIG. 4F depicts results demonstrating that no significant (NS) difference in gene expression was observed between the KG1a and KG1 cell lines. However, the PIGN gene transcriptions in all of above-mentioned samples were elevated 2- to 5-fold in comparison with PIGN gene expression in CD34+ cells from healthy individuals. Error bars represent standard deviation from the mean fold change in gene expression. FIG. 4G depicts a simplified model of the correlation of loss of PIGN protein with disease progression from a less aggressive disease stage to a more aggressive disease stage.

FIG. 5, comprising FIG. 5A and FIG. 5B depict that for TP53-independent genomic instability/DNA damage markers (H2AX and SAE2 respectively) gene expression was significantly ($p<0.05$) upregulated in the leukemic phase compared to remission phase. FIG. 5C depicts that expression of TP53-targeted apoptosis marker BAXα was downregulated in both leukemic phase and remission phase though it was more significantly ($p<0.05$) in the peripheral blood mononuclear cells (PMNC) rich with leukemic cells. FIG. 5D depicts experimental results demonstrating that the TP53 target gene involved in cell cycle control (p21) was not significantly (NS) different between the active leukemia and remission phase and could point to a TP53-independent mechanism. FIG. 5E depicts experimental results demonstrating that the TP53 deacetylase and deactivator, SIRT1 was also not significantly (NS) different between the leukemic and remission phase of disease progression. FIG. 5F depicts experimental results demonstrating that the expression of the TP53 target, TRAIL death receptor 5 (DR5) was significantly downregulated in the leukemic cell rich active leukemia phase compared to the remission phase but DR5 expression was below 50% of the normal control in both the leukemia and remission phases. Genomic instability biomarkers not regulated by TP53 (H2AX and SAE2) showed significantly transcriptional activation in mononuclear cells rich with leukemic cells in the active leukemia phase but not in mononuclear cells in the remission phase. Results were analyzed using a One-way ANOVA followed by Tukey's post hoc tests. P-values <0.05 were considered statistically significant.

FIG. 6 depicts a table showing the conserved TP53 gene mutations in both non-leukemic cells and leukemic cells.

FIG. 7, comprising FIG. 7A through FIG. 7D, depicts the TP53 gene mutation profile in leukemic and non-leukemic cells. PBMCs from patient M2 were sorted into leukemic and non-leukemic cell populations followed by Sanger sequencing of approximately 2,300 bp of DNA encoding for intron and exon regions ranging from exons 2-11 of the TP53 gene. FIG. 7A depicts the overall sequence identity in percentage of sequenced introns, and FIG. 7B depicts the same for exons, from non-leukemic and leukemic cells to the TP53 gene sequence (GenBank NC_000017.9). Statistical differences were analyzed using students t test. 'N.S.' indicates statistically non-significant (P>0.05) differences. FIG. 7C depicts the qualitative analysis of TP53 gene sequence alterations found in non-leukemic cells, and FIG. 7D depicts the same for leukemic cells, in both non-coding (intron) and coding (exon) sequences.

FIG. 8, comprising FIG. 8A through FIG. 8C, further depicts the TP53 gene mutation profile in leukemic and non-leukemic cells.

FIG. 9, comprising FIG. 9A depicts PIGN suppression (*p=0.0008) in HEK293 (TP53 wt) cells resulted in the upregulated gene expression of H2AX (p=0.0029) but no significant change (NS) in p21 gene expression. FIG. 9B depicts that PIGN suppression resulted in DNA damage response via a ~50% upregulation of γH2AX transcription and translation in HEK293 cells. FIG. 9C depicts that PIGN deletion (*p<0.0001) results in a ~15 fold increase (*p=0.0003) in H2AX gene expression but a marginal increase in TP53-dependent p21 gene expression in HEK293 cells. FIG. 9D depicts restoration of PIGN in PIGN null (CRISPR/Cas9 deletion) HEK293 cells via transfection of PIGN expression plasmid results in a marked upregulation (i.e. ~400-fold) in PIGN gene expression with a ~1.6-fold increase (p=0.0056) of H2AX transcription and no significant (NS) change in p21 gene expression. FIG. 9E depicts restoration of PIGN expression in PIGN null HEK293 cells ameliorates genomic instability as indicated by γH2AX suppression while increasing the mono-ubiquitination of H2AX which is critical in the initiation of DNA damage response. FIG. 9F and FIG. 9G depicts PIGN loss (*p=0.0003) in HL60 cells (TP53 null) results in a significant (p=0.0013) upregulation of H2AX in both transcription level (FIG. 9F) and translation level (FIG. 9G) but not (NS) p21 gene transcription. FIG. 9H depicts PIGN suppression (p=0.0019) resulted in a marginal increase (*p=0.0387) in H2AX gene expression (NS) but not p21 gene expression (NS) in K562 cells (TP53 inactivation mutation). Above-mentioned data indicated that PIGN suppression/elimination caused genomic instability was independent from TP53-pathway regulation. FIG. 9I depicts CRISPR/Cas9 ablation (***p<0.0001) of PIGN in normal healthy donor CD34+ mononuclear cells results in a significant (*p=0.0261) upregulation in H2AX transcriptional activation without a significant (NS) increase in p21 transcriptional activation. FIG. 9J depicts PIGN loss via CRISPR/Cas9 ablation induces upregulation of γH2AX translation in normal healthy donor CD34+ mononuclear cells.

FIG. 10, comprising FIG. 10A through FIG. 10K, depicts experimental results demonstrating that PIGN loss induced chromosomal instability via dysregulation of the spindle assembly checkpoint protein MAD1. FIG. 10A depicts PIGN and MAD1 were similarly expressed in a cell cycle-dependent manner with suppressed expression in the G2/M phase in HL60 and K562 cells. FIG. 10B depicts PIGN loss via CRISPR/Cas9 ablation resulted in MAD1 downregulation in normal healthy donor CD34+ mononuclear cells. FIG. 10C depicts MAD1 gene expression was significantly (***p=0.0007) impacted by PIGN gene loss in normal healthy donor CD34+ mononuclear cells. FIG. 10D depicts RNAi-mediated PIGN suppression resulted in MAD1 downregulation in K562 cells. FIG. 10E and FIG. 10F depict that when comparing PIGN wild-type (WT) HEK293 cells and PIGN null (KO) HEK293 cells respectively, PIGN loss is associated with downregulation of MAD1 protein expression and repression (*p=0.0509) of MAD1 gene transcriptional activation. FIG. 10G depicts that MAD1 suppression was accompanied by a corresponding decrease in PIGN protein expression in K562 cells. FIG. 10H demonstrates that MAD1 directly interacted with PIGN. MAD-1 was co-purified with PIGN in a HA-tag pulldown assay in PIGN null HEK293 cells. Input represents 10% of total protein lysate used in the HA pull down assay. FIG. 10I depicts PIGN loss in HEK293 cells results in phenotypes associated with chromosomal instability (increased lagging chromosomes and anaphase bridges). Shown is a quantitative analyses of missegregation errors calculated by counting the numbers of lagging and anaphase bridges observed in a total of 100 cells randomly selected from multiple fields of view. FIG. 10J depicts representative immunofluorescence images of K562 cells demonstrating that PIGN and MAD1 had a similar pattern of localization during the mitotic phase and co-localized during late prometaphase. White arrows indicate groups of chromosomes in prometaphase. Upper panel: Asynchronous cells; Lower panel: Late prometaphase cells. FIG. 10K depicts images demonstrating that PIGN loss in HEK293 cells results in phenotypes associated with chromosomal instability (increased lagging chromosomes and anaphase bridges). Depicted are representative images of missegregation errors observed in HEK293 cells, quantified in FIG. 10I. White arrows indicate lagging chromosomes and positions of anaphase bridges.

DETAILED DESCRIPTION

Figures 1, 1A:
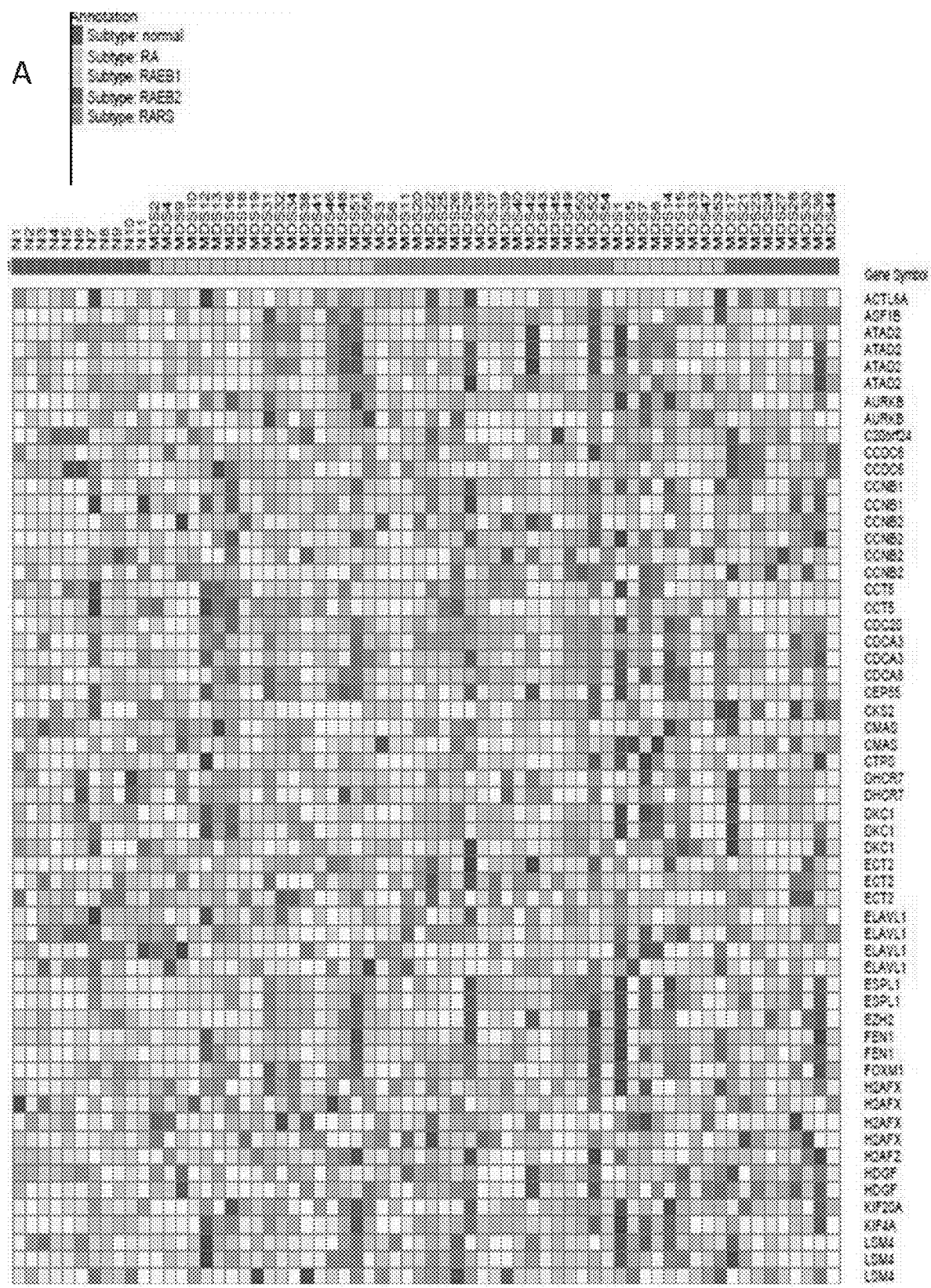
FIG. 1, comprising FIG. 1A through FIG. 1C depicts an analysis demonstrating that PIGN gene was highly ranked as a predictive biomarker of MDS risk stratification.
FIG. 1A depicts a gene expression heat map showing expression of chromosomal instability (CIN) signature from the CIN-70 gene panel was associated with MDS risk stratification in CD34+ cells isolated from bone marrow samples of 55 MDS patients and 11 normal controls (Carter et al., Nat Genet. 2006, 38:1043-1048; Pellagatti et al., Blood, 2006, 108:337-345).
Figures 1, 1A, 2:
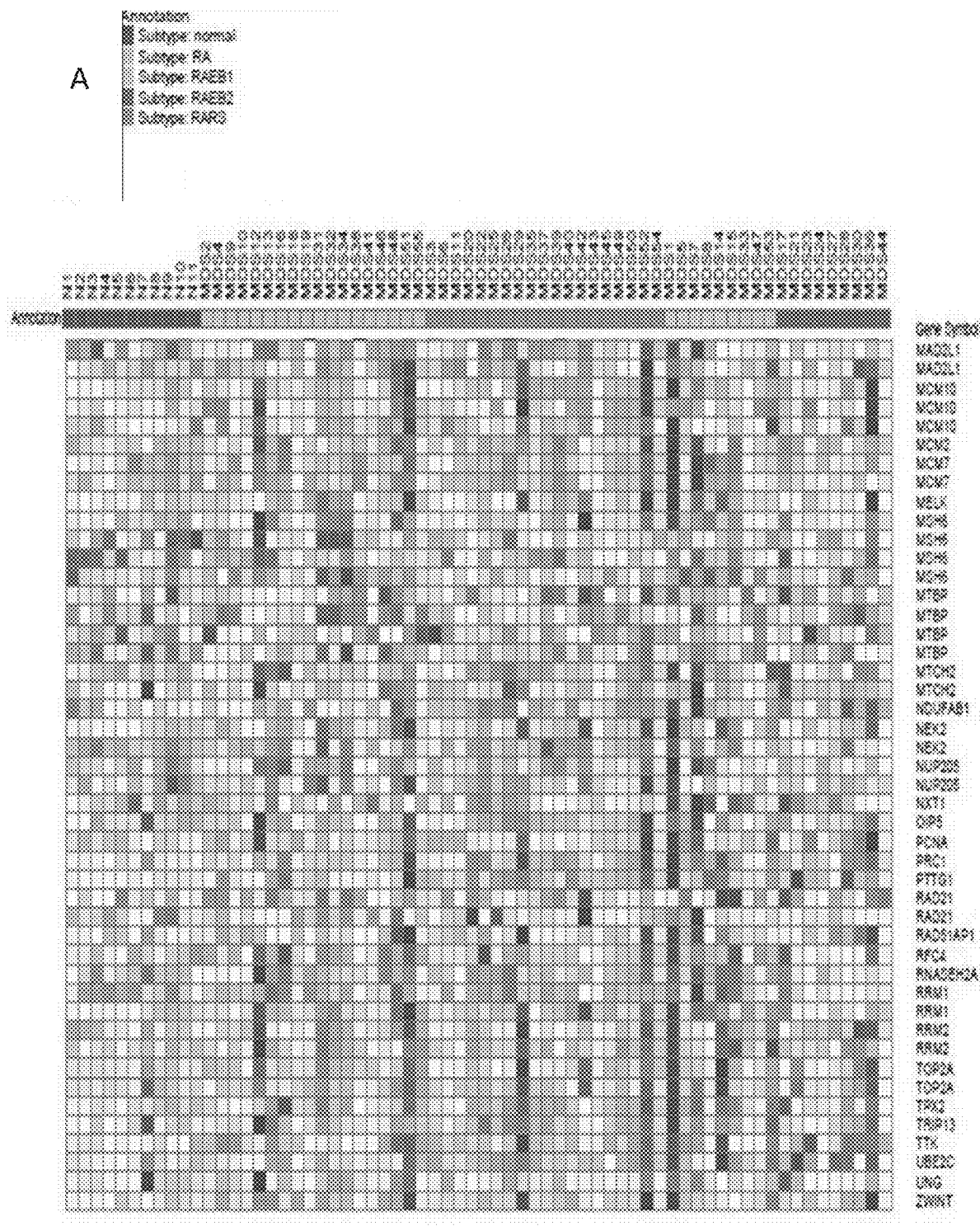
FIG. 2, comprising

The present invention is partly based upon the discovery that PIGN functions as a tumor suppressor through its role in regulating cellular genomic stability. The results presented herein demonstrate a link between PIGN gene silence/downregulation caused genomic instability and hematological neoplasia development and/or progression. That is, PIGN exhibits a protective effect on cellular genomic stability and therefore the presence of a mutated or inactivated PIGN is a prognostic indicator for cancer and/or hematological neoplasia. The results presented herein also identify MAD1 as an interacting partner of PIGN. In one embodiment, the invention further relates to the presence of a mutated or inactivated gene or gene product that PIGN interacts with as a prognostic indicator for cancer and/or hematological neoplasia. The present invention provides a method of determining the presence or absence of risk of development or progression of a hematological neoplasia and provides a method for treatment of a hematological neoplasia in patients in need thereof.

In one embodiment, the present invention is directed to methods and compositions for prognosis, treatment, inhibition, prevention, or reduction of cancer. In one embodiment, the present invention is directed to methods and compositions for prognosis, treatment, inhibition, prevention, or reduction of a hematological neoplasia. In one embodiment, the invention provides compositions and methods for modulating one or more of the level, production, and activity of PIGN.

Accordingly, the invention relates to activators (e.g., agonists) of PIGN. In one embodiment, the activator of PIGN includes but is not limited to a small molecule, a chemical compound, a protein, a peptide, a peptidomimetic, a nucleic acid, and the like.

In one embodiment, the invention provides compositions and methods for modulating one or more of the level, production, and activity of a gene or gene product PIGN interacts with. In one embodiment, a gene or gene product PIGN interacts with may be MAD1. MAD1 is a transcription factor that functions as an antagonist of MYC-mediated transcriptional activation. Therefore, in one embodiment, a composition for increasing an activity of MAD1 serves to antagonize MYC. In one embodiment, a composition for increasing an activity of MAD1 serves to sequester the MYC binding partner MAX. In one embodiment, a composition for increasing an activity of MAD1 includes but is not limited to a small molecule, a chemical compound, a protein, a peptide, a peptidomimetic, a nucleic acid, and the like.

In one embodiment, a gene or gene product PIGN interacts with may be interferon-inducible double-stranded RNA-activated protein kinase (PKR, also referred to as EIF2AK2). PKR is an interferon-inducible double-stranded RNA-activated protein kinase that may interact with PIGN during the cell cycle. Therefore, in one embodiment, the invention relates to modulating one or more of the level, production, and activity of PKR. In one embodiment, the invention relates to a method of decreasing one or more of the level, production, and activity of PKR.

The invention also relates to activators and inhibitors (e.g. antagonists) of genes or gene products that regulate PIGN, an activity of PIGN, a gene or gene product that PIGN interacts with, an activity of gene or gene product that PIGN interacts with or a combination thereof. In one embodiment, the activator or inhibitor of a regulatory gene or protein includes but is not limited to a small molecule, a chemical compound, a protein, a peptide, a peptidomimetic, a nucleic acid, and the like.

In one embodiment, the present invention comprises a method for increasing one or more of the level, production, and activity of PIGN comprising administering to a subject an effective amount of a composition comprising an activator of PIGN. In one embodiment, the present invention comprises a method for increasing one or more of the level, production, and activity of PIGN comprising administering to a subject an effective amount of a composition comprising an activator or inhibitor of a gene or gene product that PIGN interacts with. In one embodiment, the present invention comprises a method for increasing one or more of the level, production, and activity of PIGN comprising administering to a subject an effective amount of a composition comprising an activator or inhibitor of a regulator of PIGN. In an embodiment of the present invention, the composition increases the transcription of PIGN or translation of PIGN mRNA. In one embodiment of the present invention, the composition increases the transcription or translation of mRNA of a gene or gene product PIGN interacts with. In one embodiment of the present invention, the composition decreases the transcription or translation of mRNA of a gene or gene product PIGN interacts with. In one embodiment of the present invention, the composition results in an increase in the activity of PIGN.

In one embodiment, the present invention comprises a method for increasing one or more of the level, production, and activity of MAD1 comprising administering to a subject an effective amount of a composition comprising an activator of MAD1. In one embodiment, the present invention comprises a method for increasing one or more of the level, production, and activity of MAD1 comprising administering to a subject an effective amount of a composition comprising an activator or inhibitor of a gene or gene product that MAD1 interacts with. In one embodiment, the present invention comprises a method for increasing one or more of the level, production, and activity of MAD1 comprising administering to a subject an effective amount of a composition comprising an activator or inhibitor of a regulator of MAD1. In an embodiment of the present invention, the composition increases the transcription of MAD1 or translation of MAD1 mRNA. In one embodiment of the present invention, the composition increases the transcription or translation of mRNA of a gene or gene product MAD1 interacts with. In one embodiment of the present invention, the composition decreases the transcription or translation of mRNA of a gene or gene product MAD1 interacts with. In one embodiment of the present invention, the composition results in an increase in the activity of MAD1.

In one embodiment, the present invention comprises a method for decreasing one or more of the level, production, and activity of PKR comprising administering to a subject an effective amount of a composition comprising an inhibitor of PKR. In one embodiment, the present invention comprises a method for decreasing one or more of the level, production, and activity of PKR comprising administering to a subject an effective amount of a composition comprising an activator or inhibitor of a gene or gene product that PKR interacts with. In one embodiment, the present invention comprises a method for increasing one or more of the level, production, and activity of PKR comprising administering to a subject an effective amount of a composition comprising an activator or inhibitor of a regulator of PKR. In an embodiment of the present invention, the composition decreases the transcription of PKR or translation of PKR mRNA. In one embodiment of the present invention, the composition results in a decrease in the activity of PKR.

Another aspect of the present invention comprises a pharmaceutical composition comprising the modulators (e.g., activators or inhibitors) of PIGN, MAD1, PKR, an activity of PIGN, an activity of MAD1, an activity of PKR, a gene product that PIGN interacts with, a gene product that MAD1 interacts with, a gene product that PKR interacts with, or a combination thereof. In one embodiment, the composition of the invention can be used in combination with other therapeutic agents.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20%, ±10%, ±5%, ±1%, or ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

The term "activate," as used herein, means to induce or increase an activity or function, for example, about ten percent relative to a control value. Preferably, the activity is induced or increased by 50% compared to a control value, more preferably by 75%, and even more preferably by 95%. "Activate," as used herein, also means to increase a molecule, a reaction, an interaction, a gene, a mRNA, and/or a protein's expression, stability, function or activity by a measurable amount or to increase entirely. Activators are compounds that, e.g., bind to, partially or totally induce stimulation, increase, promote, induce activation, activate, sensitize, or up regulate a protein, a gene, and an mRNA stability, expression, function and activity, e.g., agonists.

As used herein the terms "alteration," "defect," "variation," or "mutation," refers to a mutation in a gene in a cell that affects the function, activity, expression (transcription or translation) or conformation of the polypeptide that it encodes. Mutations encompassed by the present invention can be any mutation of a gene in a cell that results in the enhancement or disruption of the function, activity, expression or conformation of the encoded polypeptide, including the complete absence of expression of the encoded protein and can include, for example, missense and nonsense mutations, insertions, deletions, frameshifts and premature terminations. Without being so limited, mutations encompassed by the present invention may alter splicing the mRNA (splice site mutation) or cause a shift in the reading frame (frameshift).

The term "amplification" refers to the operation by which the number of copies of a target nucleotide sequence present in a sample is multiplied.

An "anti-tumor effect" can also be manifested by the ability of the agents, peptides, polynucleotides, cells and antibodies of the invention in prevention of the occurrence of tumor in the first place or in treatment of existing tumor.

As used herein, "biomarker" in the context of the present invention encompasses, without limitation, proteins, nucleic acids, and metabolites, together with their polymorphisms, mutations, variants, modifications, subunits, fragments, protein-ligand complexes, and degradation products, protein-ligand complexes, elements, related metabolites, and other analytes or sample-derived measures. Biomarkers can also include mutated proteins or mutated nucleic acids. Biomarkers also encompass non-blood borne factors or non-analyte physiological markers of health status, such as clinical parameters, as well as traditional laboratory risk factors. Biomarkers also include any calculated indices created mathematically or combinations of any one or more of the foregoing measurements, including temporal trends and differences.

The term "cancer" as used herein is defined as disease characterized by the abnormal growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer, sarcoma and the like.

"Coding sequence" or "encoding nucleic acid" as used herein may refer to the nucleic acid (RNA or DNA molecule) that comprise a nucleotide sequence which encodes an antigen set forth herein. The coding sequence may further include initiation and termination signals operably linked to regulatory elements including a promoter and polyadenylation signal capable of directing expression in the cells of an individual or mammal to whom the nucleic acid is administered. The coding sequence may further include sequences that encode signal peptides.

The term "control" or "reference standard" describes a material comprising none, or a normal, low, or high level of one of more of the marker (or biomarker) expression products of one or more the markers (or biomarkers) of the invention, such that the control or reference standard may serve as a comparator against which a sample can be compared.

As used herein, the term "data" in relation to one or more biomarkers, or the term "biomarker data" generally refers to data reflective of the absolute and/or relative abundance (level) of a product of a biomarker in a sample. As used herein, the term "dataset" in relation to one or more biomarkers refers to a set of data representing levels of each of one or more biomarker products of a panel of biomarkers in a reference population of subjects. A dataset can be used to generate a formula/classifier of the invention. According to one embodiment, the dataset need not comprise data for each biomarker product of the panel for each individual of the reference population. For example, the "dataset" when used in the context of a dataset to be applied to a formula can refer to data representing levels of products of each biomarker for each individual in one or more reference populations, but as would be understood can also refer to data representing levels of products of each biomarker for 99%, 95%, 90%, 85%, 80%, 75%, 70% or less of the individuals in each of said one or more reference populations and can still be useful for purposes of applying to a formula.

By the phrase "determining the level of marker (or biomarker) expression" is meant an assessment of the degree of expression of a marker in a sample at the nucleic acid or protein level, using technology available to the skilled artisan to detect a sufficient portion of any marker expression product.

"Differentially decreased expression" or "down regulation" refers to biomarker product levels which are at least 10% or more, for example, 20%, 30%, 40%, or 50%, 60%, 70%, 80%, 90% lower or less, and/or 2.0 fold, 1.8 fold, 1.6 fold, 1.4 fold, 1.2 fold, 1.1 fold or less lower, and any and all whole or partial increments therebetween than a control.

"Differentially increased expression" or "up regulation" refers to biomarker product levels which are at least 10% or more, for example, 20%, 30%, 40%, or 50%, 60%, 70%, 80%, 90% higher or more, and/or 1.1 fold, 1.2 fold, 1.4 fold, 1.6 fold, 1.8 fold, 2.0 fold higher or more, and any and all whole or partial increments therebetween than a control.

A "disease" is a state of health of an animal wherein the animal cannot maintain homeostasis, and wherein if the disease is not ameliorated then the animal's health continues to deteriorate.

The "level" of one or more biomarkers means the absolute or relative amount or concentration of the biomarker in the sample.

A "marker," as the term is used herein, refers to a molecule that can be detected. Therefore, a marker according to the present invention includes, but is not limited to, a nucleic acid, a polypeptide, a carbohydrate, a lipid, an inorganic molecule, an organic molecule, or a radiolabel, each of which may vary widely in size and properties. A "marker" as used herein can also mean a "biomarker." A "marker" can be detected using any means known in the art or by a previously unknown means that only becomes apparent upon consideration of the marker by the skilled artisan. A marker may be detected using a direct means, or by a method including multiple steps of intermediate processing and/or detection. The term "tag" is also used interchangeably with the term "marker," but the term "tag" may also be used, in certain aspects, to include markers that are associated with one or more other molecules.

The term "marker (or biomarker) expression" as used herein, encompasses the transcription, translation, post-translation modification, and phenotypic manifestation of a gene, including all aspects of the transformation of information encoded in a gene into RNA or protein. By way of non-limiting example, marker expression includes transcription into messenger RNA (mRNA) and translation into protein, as well as transcription into types of RNA such as transfer RNA (tRNA) and ribosomal RNA (rRNA) that are not translated into protein.

The terms "microarray" and "array" refers broadly to both "DNA microarrays" and "DNA chip(s)," and encompasses all art-recognized solid supports, and all art-recognized methods for affixing nucleic acid molecules thereto or for synthesis of nucleic acids thereon. Preferred arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 5,800,992, 6,040,193, 5,424,186 and Fodor et al., 1991, Science, 251:767-777, each of which is incorporated by reference in its entirety for all purposes. Arrays may generally be produced using a variety of techniques, such as mechanical synthesis methods or light directed synthesis methods that incorporate a combination of photolithographic methods and solid phase synthesis methods. Techniques for the synthesis of these arrays using mechanical synthesis methods are described in, e.g., U.S. Pat. Nos. 5,384,261, and 6,040,193, which are incorporated herein by reference in their entirety for all purposes. Although a planar array surface is preferred, the array may be fabricated on a surface of virtually any shape or even a multiplicity of surfaces. Arrays may be nucleic acids on beads, gels, polymeric surfaces, fibers such as fiber optics, glass or any other appropriate substrate. (See U.S. Pat. Nos. 5,770,358, 5,789, 162, 5,708,153, 6,040,193 and 5,800,992, which are hereby incorporated by reference in their entirety for all purposes.) Arrays may be packaged in such a manner as to allow for diagnostic use or can be an all-inclusive device; e.g., U.S. Pat. Nos. 5,856,174 and 5,922,591 incorporated in their entirety by reference for all purposes. Arrays are commercially available from, for example, Affymetrix (Santa Clara, Calif.) and Applied Biosystems (Foster City, Calif.), and are directed to a variety of purposes, including genotyping, diagnostics, mutation analysis, marker expression, and gene expression monitoring for a variety of eukaryotic and prokaryotic organisms. The number of probes on a solid support may be varied by changing the size of the individual features. In one embodiment the feature size is 20 by 25 microns square, in other embodiments features may be, for example, 8 by 8, 5 by 5 or 3 by 3 microns square, resulting in about 2,600,000, 6,600,000 or 18,000,000 individual probe features.

"Measuring" or "measurement," or alternatively "detecting" or "detection," means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's clinical parameters.

By the term "modulating," as used herein, is meant mediating a detectable increase or decrease in the activity and/or level of a mRNA, polypeptide, or a response in a subject compared with the activity and/or level of a mRNA, polypeptide or a response in the subject in the absence of a treatment or compound, and/or compared with the activity and/or level of a mRNA, polypeptide, or a response in an otherwise identical but untreated subject.

"Operably linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV 40 late promoter and the CMV IE promoter.

As used herein, the term "providing a prognosis" refers to providing a prediction of the probable course and outcome of a disease, including prediction of severity, duration, chances of recovery, etc. The methods can also be used to devise a suitable therapeutic plan, e.g., by indicating whether or not the condition is still at an early stage or if the condition has advanced to a stage where aggressive therapy would be ineffective.

"Polypeptide," as used herein refers to a polymer in which the monomers are amino acid residues which are joined together through amide bonds. When the amino acids are alpha-amino acids, either the L-optical isomer or the D-optical isomer can be used, the L-isomers being preferred. The terms "polypeptide" or "protein" or "peptide" as used herein are intended to encompass any amino acid sequence and include modified sequences such as glycoproteins.

The term "polypeptide" or "protein" or "peptide" is specifically intended to cover naturally occurring proteins, as well as those which are recombinantly or synthetically produced. It should be noted that the term "polypeptide" or "protein" includes naturally occurring modified forms of the proteins, such as glycosylated forms.

A "reference level" of a biomarker means a level of the biomarker that is indicative of a particular disease state, phenotype, or lack thereof, as well as combinations of disease states, phenotypes, or lack thereof. A "positive" reference level of a biomarker means a level that is indicative of a particular disease state or phenotype. A "negative" reference level of a biomarker means a level that is indicative of a lack of a particular disease state or phenotype.

The term "regulating" as used herein can mean any method of altering the level or activity of a substrate. Non-limiting examples of regulating with regard to a protein include affecting expression (including transcription and/or translation), affecting folding, affecting degradation or protein turnover, and affecting localization of a protein. Non-limiting examples of regulating with regard to an enzyme further include affecting the enzymatic activity. "Regulator" refers to a molecule whose activity includes affecting the level or activity of a substrate. A regulator can be direct or indirect. A regulator can function to activate or inhibit or otherwise modulate its substrate.

The term "risk stratification," according to the invention, comprises finding a patient, with the worse prognosis, for the purpose of intensive diagnosis and therapy/treatment of a disease, with the goal of allowing as advantageous a course of the disease as possible.

"Sample", "specimen" or "biological sample" as used herein means a biological material isolated from an individual. The biological sample may contain any biological material suitable for detecting the desired biomarkers, and may comprise cellular and/or non-cellular material obtained from the individual.

"Treatment" or "treating," as used herein can mean protecting of an animal from a disease through means of preventing, suppressing, repressing, or completely eliminating the disease. "Treatment" as used herein can also include counseling on the risk of a course of action or inaction or monitoring a disease for progression.

As used herein, the terms "therapy" or "therapeutic regimen" refer to those activities taken to alleviate or alter a disorder or disease state, e.g., a course of treatment intended to reduce or eliminate at least one sign or symptom of a disease or disorder using pharmacological, surgical, dietary and/or other techniques. A therapeutic regimen may include a prescribed dosage of one or more drugs or surgery. Therapies will most often be beneficial and reduce or eliminate at least one sign or symptom of the disorder or disease state, but in some instances the effect of a therapy will have non-desirable or side-effects. The effect of therapy will also be impacted by the physiological state of the subject, e.g., age, gender, genetics, weight, other disease conditions, etc.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

"Truncation" as used herein can be a coding sequence of a nucleic acid molecule wherein there is a mutation encoding a premature stop codon. "Truncation" can also be the portion of a protein that is produced from the translation of a nucleic acid molecule wherein there is a mutation encoding a premature stop codon.

"Variant" as the term is used herein, is a nucleic acid sequence or a peptide sequence that differs in sequence from a reference nucleic acid sequence or peptide sequence respectively, but retains essential properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

"Vector" as used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

As used herein, the term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and/or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention is partly based upon the discovery that PIGN exhibits a protective effect on cellular genomic stability and further identifies MAD1 as an interacting partner of PIGN. Therefore, the presence of a mutated or inactivated PIGN or MAD1 is a prognostic indicator for cancer and/or hematological neoplasia. The present invention provides a method of determining the presence or absence of risk of development or progression of a hematological neoplasia and provides a method for treatment of a hematological neoplasia in patients in need thereof.

In one embodiment, a hematological neoplasia is a hematological cancer. In one embodiment, a hematological cancer is an acute leukemia. In one embodiment, an acute leukemia is one of acute myeloid leukemia (AML) and acute lymphoblastic leukemia (ALL). In one embodiment, a hematological cancer is a chronic leukemia. In one embodiment, a chronic leukemia is one of chronic myeloid leukemia (CML), chronic lymphocytic leukemia (CLL), Hodgkin Lymphoma and non-Hodgkin lymphoma. In one embodiment, a hematological neoplasia is a preleukemic state. In one embodiment, a preleukemic state is one of Myelodysplastic syndrome (MDS) and lymphoproliferative disorders (LPD). In one embodiment, the hematological neoplasia is therapy-associated.

In one embodiment, the biomarker that can serve as a prognostic indicator for individuals with a hematological neoplasia is a phosphatidylinositol glycan anchor biosynthesis protein. In one embodiment, the biomarker is a DNA or RNA molecule encoding a phosphatidylinositol glycan anchor biosynthesis protein. In one embodiment, the biomarker is a DNA or RNA molecule encoding a variant of a phosphatidylinositol glycan anchor biosynthesis protein.

In one embodiment, the phosphatidylinositol glycan anchor biosynthesis protein is one or more of PIGA, PIGH, PIGF, PIGC, PIGQ, PIGL, PIGB, PIGW, PIGX, PIGU, PIGT, PIGO, PIGN, PIGM, PIGS, PIGV, PIGZ, PIGG, PIGY, and PIGK. In an exemplary embodiment, the phosphatidylinositol glycan anchor biosynthesis protein is PIGN. In one embodiment, the biomarker is a DNA or RNA molecule encoding a PIGN. In one embodiment, the biomarker is a DNA or RNA molecule encoding a variant of PIGN.

In one embodiment, the biomarker that can serve as a prognostic indicator for individuals with a hematological neoplasia is a gene or gene product that PIGN interacts with. In one embodiment, a gene or gene product that PIGN interacts with is the MXD1 gene, encoding Mitotic spindle assembly checkpoint protein MAD1. In one embodiment, the biomarker is a DNA or RNA molecule encoding MAD1. In one embodiment, the biomarker is a DNA or RNA molecule encoding a variant of MAD1.

In one embodiment, a prognostic indicator for hematological neoplasia is a reduction in function of one or more biomarkers of the invention. In one embodiment, the transcription of a biomarker is inhibited resulting in the reduction or loss of function. In one embodiment, synthesis of a biomarker is inhibited resulting in the reduction or loss of function. In one embodiment a biomarker protein is mutated resulting in a reduction or loss of function. In one embodiment, a mutation in a biomarker is a truncation due to a premature stop codon.

In one embodiment, a mutation in a biomarker is in the genome of an individual. In one embodiment, a mutation is somatic. In one embodiment, a mutation is in a sub-population of cells. In one embodiment, the mutation is therapy-related. In one embodiment, a therapy-related mutation arose due to exposure to prior chemotherapeutic or radiation treatment.

In one embodiment, reduction in function of a phosphatidylinositol glycan anchor biosynthesis protein is causative of a reduction in cellular glycosylphosphatidylinositol (GPI)-anchored proteins. In one embodiment, a prognostic indicator for individuals with a hematological neoplasia is the frequency of one or more GPI-anchored proteins in a sample, or the GPI-AP deficiency frequency. In one embodiment, the GPI-anchored protein is one or more of 1G7, 5'-nucleotidase, acetylcholinesterase, alkaline phosphatase, CAPRIN1, CD14, CD16, CD16b, CD52, CD55, CD59, CEA, dipeptidase, folate-binding protein, FOLR1, LFA-3, NCAM, PH-20, procyclin, Qa-2, scrapie prion protein, Thy-1, and VSG.

In one embodiment, reduction in function of MAD1 is causative of an increase in MYC-mediated translational activation. In one embodiment, a prognostic indicator for individuals with a hematological neoplasia is an increase in MYC-mediated translational activation.

Identifying a Marker or Biomarker

The invention includes methods for the detection of a biomarker in normal individuals and individuals with a hematological neoplasia, and use of the biomarker as a prognostic or diagnostic indicator for development or progression of hematological neoplasia.

The invention contemplates the using methods known to those skilled in the art to detect and to measure the level of differentially expressed markers, such as RNA and protein, to measure the level of one or more differentially expressed markers.

Methods of detecting or measuring gene expression may utilize methods that focus on cellular components (cellular examination), or methods that focus on examining extracellular components (fluid examination). Because gene expression involves the ordered production of a number of different molecules, a cellular or fluid examination may be used to detect or measure a variety of molecules including RNA, protein, and a number of molecules that may be modified as a result of the protein's function. Typical diagnostic methods focusing on nucleic acids include amplification techniques such as PCR and RT-PCR (including quantitative variants), and hybridization techniques such as in situ hybridization, microarrays, blots, and others. Typical diagnostic methods focusing on proteins include binding techniques such as ELISA, immunohistochemistry, microarray and functional techniques such as enzymatic assays.

The genes identified as being differentially expressed may be assessed in a variety of nucleic acid detection assays to detect or quantify the expression level of a gene or multiple genes in a given sample. For example, traditional Northern blotting, nuclease protection, RT-PCR, microarray, and differential display methods may be used for detecting gene expression levels. Methods for assaying for mRNA include Northern blots, slot blots, dot blots, and hybridization to an ordered array of oligonucleotides. Any method for specifically and quantitatively measuring a specific protein or mRNA or DNA product can be used. However, methods and assays are most efficiently designed with array or chip hybridization-based methods for detecting the expression of a large number of genes. Any hybridization assay format may be used, including solution-based and solid support-based assay formats.

The protein products of the genes identified herein can also be assayed to determine the amount of expression. Methods for assaying for a protein include Western blot, immunoprecipitation, and radioimmunoassay. The proteins analyzed may be localized intracellularly (most commonly an application of immunohistochemistry) or extracellularly (most commonly an application of immunoassays such as ELISA). The proteins analyzed may be soluble or GPI-anchored to a cell membrane. In one embodiment, the fraction of a protein in soluble as compared to GPI-anchored form is a prognostic or diagnostic indicator for hematological neoplasia.

Biological samples may be of any biological tissue or fluid containing saliva. Frequently the sample will be a "clinical sample" which is a sample derived from a patient.

Controls groups may either be normal or samples from known stages of hematological neoplasia. As described below, comparison of the protein level of a biomarker of the sample to be tested with that of a control sample can be used as a prognostic indicator for hematological neoplasia. In some instances, the control groups are only for the purposes of establishing initial cutoffs for the assays of the invention. Therefore, in some instances, the systems and methods of the invention can provide prognostic or diagnostic indicators for hematological neoplasia without the need to compare with a control group.

Methods of Diagnosis

The present invention relates to the identification of biomarkers associated with MDS, AML and/or hematological neoplasia. Accordingly, the present invention features methods for identifying subjects who are currently diagnosed with a hematological neoplasia but are at risk of advancement to AML. These biomarkers are also useful for monitoring subjects undergoing treatments and therapies for genomic instability or cancer related conditions, for monitoring subjects who have developed a hematological neoplasia as a result of treatments and therapies for genomic instability or cancer related conditions and for selecting or modifying therapies and treatments in the above individuals wherein selection and use of such treatments and therapies reduces the risk of development or progression of a hematological neoplasia.

Identifying a subject before they develop AML enables the selection and initiation of various therapeutic interventions or treatment regimens in order to delay, reduce or prevent that subject's conversion to a disease state. Subjects identified as having an increased risk of MDS, AML and/or hematological neoplasia conditions can optionally be advised about increased risk of chemotherapeutic and or radiation based interventions and recommended alternative treatments, if available, to mitigate the risk of development of MDS, AML and/or hematological neoplasia.

The invention provides improved diagnosis and prognosis of MDS, AML and/or hematological neoplasia. The risk of developing MDS, AML and/or hematological neoplasia conditions can be assessed by measuring one or more of the biomarkers described herein, and comparing the measured values to reference or index values. Such a comparison can be undertaken with mathematical algorithms or formula in order to combine information from results of multiple individual biomarkers and other parameters into a single measurement or index.

The biomarkers of the present invention can thus be used to generate a biomarker profile or signature of subjects: (i) who do not have and are not expected to develop MDS, AML and/or hematological neoplasia and/or (ii) who have or are expected to develop MDS, AML and/or hematological neoplasia. The biomarker profile of a subject can be compared to a predetermined or reference biomarker profile to diagnose or identify subjects at risk for developing MDS, AML and/or hematological neoplasia, to monitor the progression of disease, as well as the rate of progression of disease, and to monitor the effectiveness MDS, AML and/or hematological neoplasia treatments. Data concerning the biomarkers of the present invention can also be combined or correlated with other data or test results, such as, without limitation, measurements of clinical parameters or other algorithms for MDS, AML and/or hematological neoplasia. Other data includes age, ethnicity, sex, previous cancer treatment, exposure to radiation, chemical exposure, smoking, and other blood or genetic disorders. The machine-readable media can also comprise subject information such as medical history and any relevant family history.

The present invention also provides methods for identifying agents for treating MDS, AML and/or hematological neoplasia that are appropriate or otherwise customized for a specific subject. In this regard, a test sample from a subject can be taken before and after a treatment (e.g. exposure to a gene therapy), and the level of one or more biomarkers can be determined. The level of one or more biomarkers can be compared to samples derived from one or more subjects who have shown improvements in risk factors as a result of such treatment or exposure.

In various embodiments, methods are disclosed herein that may be of use to determine whether a subject has or is at risk of developing a hematological neoplasia, for instance MDS or AML. In some embodiments, these methods may utilize a biological sample (such as urine, saliva, blood, serum, amniotic fluid, or tears), for the detection of one or more markers of the invention in the sample.

In one embodiment, the method comprises detecting one or more markers in a biological sample of the subject. In various embodiments, the level of one or more of markers of the invention in the biological sample of the subject is compared with the level of a corresponding biomarker in a comparator. Non-limiting examples of comparators include, but are not limited to, a negative control, a positive control, an expected normal background value of the subject, a historical normal background value of the subject, an expected normal background value of a population that the subject is a member of, or a historical normal background value of a population that the subject is a member of.

In another embodiment, the invention is a method of monitoring the progression of a hematological neoplasia in a subject by assessing the level of one or more of the markers of the invention in a biological sample of the subject.

In various embodiments, the subject is a human subject, and may be of any race, sex and age.

Information obtained from the methods of the invention described herein can be used alone, or in combination with other information (e.g., disease status, disease history, vital signs, blood chemistry, etc.) from the subject or from the biological sample obtained from the subject.

In various embodiments of the methods of the invention, the level of one or more markers of the invention is determined to be decreased when the level of one or more of the markers of the invention is decreased by at least 10%, by at least 20%, by at least 30%, by at least 40%, by at least 50%, by at least 60%, by at least 70%, by at least 80%, by at least 90%, or by at least 100%, when compared to with a comparator control.

In other various embodiments of the methods of the invention, the level of one or more markers of the invention is determined to be increased when the level of one or more of the markers of the invention is increased by at least 10%, by at least 20%, by at least 30%, by at least 40%, by at least 50%, by at least 60%, by at least 70%, by at least 80%, by at least 90%, or by at least 100%, when compared to with a comparator control.

In the methods of the invention, a biological sample from a subject is assessed for the level of one or more of the markers of the invention in the biological sample obtained from the patient. The level of one or more of the markers of the invention in the biological sample can be determined by assessing the amount of polypeptide of one or more of the biomarkers of the invention in the biological sample, the amount of mRNA of one or more of the biomarkers of the invention in the biological sample, the amount of enzymatic activity of one or more of the biomarkers of the invention in the biological sample, or a combination thereof.

Detecting a Biomarker

Biomarkers generally can be measured and detected through a variety of assays, methods and detection systems known to one of skill in the art. Various methods include but are not limited to refractive index spectroscopy (RI), ultraviolet spectroscopy (UV), fluorescence analysis, electrochemical analysis, radiochemical analysis, near-infrared spectroscopy (near-IR), infrared (IR) spectroscopy, nuclear magnetic resonance spectroscopy (NMR), light scattering analysis (LS), mass spectrometry, pyrolysis mass spectrometry, nephelometry, dispersive Raman spectroscopy, gas chromatography, liquid chromatography, gas chromatography combined with mass spectrometry, liquid chromatography combined with mass spectrometry, matrix-assisted laser desorption ionization-time of flight (MALDI-TOF) combined with mass spectrometry, ion spray spectroscopy combined with mass spectrometry, capillary electrophoresis, colorimetry and surface plasmon resonance (such as according to systems provided by Biacore Life Sciences). See also PCT Publications WO/2004/056456 and WO/2004/088309. In this regard, biomarkers can be measured using the above-mentioned detection methods, or other methods known to the skilled artisan. Other biomarkers can be similarly detected using reagents that are specifically designed or tailored to detect them.

Different types of biomarkers and their measurements can be combined in the compositions and methods of the present invention. In various embodiments, the protein form of the biomarkers is measured. In various embodiments, the nucleic acid form of the biomarkers is measured. In exemplary embodiments, the nucleic acid form is mRNA. In various embodiments, measurements of protein biomarkers are used in conjunction with measurements of nucleic acid biomarkers.

Methods for detecting mRNA, such as RT-PCR, real time PCR, branch DNA, NASBA and others, are well known in the art. Using sequence information provided by the database entries for the biomarker sequences, expression of the biomarker sequences can be detected (if present) and measured using techniques well known to one of ordinary skill in the art. For example, sequences in sequence database entries or sequences disclosed herein can be used to construct probes for detecting biomarker RNA sequences in, e.g., Northern blot hybridization analyses or methods which specifically, and, preferably, quantitatively amplify specific nucleic acid sequences. As another example, the sequences can be used to construct primers for specifically amplifying the biomarker sequences in, e.g., amplification-based detection methods such as reverse-transcription based polymerase chain reaction (RT-PCR). When alterations in gene expression are associated with gene amplification, deletion, polymorphisms and mutations, sequence comparisons in test and reference populations can be made by comparing relative amounts of the examined DNA sequences in the test and reference cell populations. In addition to Northern blot and RT-PCR, RNA can also be measured using, for example, other target amplification methods (e.g., TMA, SDA, NASBA), signal amplification methods (e.g., bDNA), nuclease protection assays, in situ hybridization and the like.

The 'level' or concentration of the biomarker in a sample may be determined by any suitable assay. A suitable assay may include one or more of the following methods, an enzyme assay, an immunoassay, mass spectrometry, chromatography, electrophoresis or an antibody microarray, or any combination thereof. Thus, as would be understood by one skilled in the art, the system and methods of the invention may include any method known in the art to detect a biomarker in a sample.

The invention described herein also relates to methods for a multiplex analysis platform. In one embodiment, the method comprises an analytical method for multiplexing analytical measurements of markers. In another embodiment, the method comprises a set of compatible analytical strategies for multiplex measurements of markers and/or metabolites in a sample.

Kits

The present invention also pertains to kits useful in the methods of the invention. Such kits comprise various combinations of components useful in any of the methods described elsewhere herein, including for example, materials for quantitatively analyzing a biomarker of the invention (e.g., polypeptide and/or nucleic acid), materials for assessing the activity of a biomarker of the invention (e.g., polypeptide and/or nucleic acid), and instructional material. For example, in one embodiment, the kit comprises components useful for the quantification of a desired polypeptide in a biological sample.

In a further embodiment, the kit comprises the components of an assay for monitoring the effectiveness of a treatment administered to a subject in need thereof, containing instructional material and the components for determining whether the level of a biomarker of the invention in a biological sample obtained from the subject is modulated during or after administration of the treatment. In various embodiments, to determine whether the level of a biomarker of the invention is modulated in a biological sample obtained from the subject, the level of the biomarker is compared with the level of at least one comparator control contained in the kit, such as a positive control, a negative control, a historical control, a historical norm, or the level of another reference molecule in the biological sample. In certain embodiments, the ratio of the biomarker and a reference molecule is determined to aid in the monitoring of the treatment.

Treatments

In one embodiment, the present invention provides methods for treatment, inhibition, prevention, or reduction of a hematological neoplasia using a modulator of PIGN. In one embodiment, the modulator is an activator of PIGN. In one embodiment, the modulator is an activator or inhibitor of a gene or gene product that PIGN interacts with. In one embodiment, the modulator is an inhibitor of a regulator of PIGN function. In one embodiment, the modulator serves to increase PIGN function.

In one embodiment, the present invention provides methods for treatment, inhibition, prevention, or reduction of a hematological neoplasia using a modulator of MAD1. In one embodiment, the modulator is an activator of MAD1. In one embodiment, the modulator is an activator or inhibitor of a gene or gene product that MAD1 interacts with. In one embodiment, the modulator is an inhibitor of a regulator of MAD1 function. In one embodiment, the modulator serves to increase MAD1 function.

One aspect of the invention provides a method of treating or preventing cancer using an activator of the invention. The following are non-limiting examples of cancers that can be treated by the disclosed methods and compositions: Acute Lymphoblastic; Acute Myeloid Leukemia; Adrenocortical Carcinoma; Adrenocortical Carcinoma, Childhood; Appendix Cancer; Basal Cell Carcinoma; Bile Duct Cancer, Extrahepatic; Bladder Cancer; Bone Cancer; Osteosarcoma and Malignant Fibrous Histiocytoma; Brain Stem Glioma, Childhood; Brain Tumor, Adult; Brain Tumor, Brain Stem Glioma, Childhood; Brain Tumor, Central Nervous System Atypical Teratoid/Rhabdoid Tumor, Childhood; Central Nervous System Embryonal Tumors; Cerebellar Astrocytoma; Cerebral Astrocytotna/Malignant Glioma; Craniopharyngioma; Ependymoblastoma; Ependymoma; Medulloblastoma; Medulloepithelioma; Pineal Parenchymal Tumors of intermediate Differentiation; Supratentorial Primitive Neuroectodermal Tumors and Pineoblastoma; Visual Pathway and Hypothalamic Glioma; Brain and Spinal Cord Tumors; Breast Cancer; Bronchial Tumors; Burkitt Lymphoma; Carcinoid Tumor; Carcinoid Tumor, Gastrointestinal; Central Nervous System Atypical Teratoid/Rhabdoid Tumor; Central Nervous System Embryonal Tumors; Central Nervous System Lymphoma; Cerebellar Astrocytoma Cerebral Astrocytoma/Malignant Glioma, Childhood; Cervical Cancer; Chordoma, Childhood; Chronic Lymphocytic Leukemia; Chronic Myelogenous Leukemia; Chronic Myeloproliferative Disorders; Colon Cancer; Colorectal Cancer; Craniopharyngioma; Cutaneous T-Cell Lymphoma; Esophageal Cancer; Ewing Family of Tumors; Extragonadal Germ Cell Tumor; Extrahepatic Bile Duct Cancer; Eye Cancer, intraocular Melanoma; Eye Cancer, Retinoblastoma; Gallbladder Cancer; Gastric (Stomach) Cancer; Gastrointestinal Carcinoid Tumor; Gastrointestinal Stromal Tumor (GIST); Germ Cell Tumor, Extracranial; Germ Cell Tumor, Extragonadal; Germ Cell Tumor, Ovarian; Gestational Trophoblastic Tumor; Glioma; Glioma, Childhood Brain Stem; Glioma, Childhood Cerebral Astrocytoma; Glioma, Childhood Visual Pathway and Hypothalamic; Hairy Cell Leukemia; Head and Neck Cancer; Hepatocellular (Liver) Cancer; Histiocytosis, Langerhans Cell; Hodgkin Lymphoma; Hypopharyngeal Cancer; Hypothalamic and Visual Pathway Glioma; intraocular Melanoma; Islet Cell Tumors; Kidney (Renal Cell) Cancer; Langerhans Cell Histiocytosis; Laryngeal Cancer; Leukemia, Acute Lymphoblastic; Leukemia, Acute Myeloid; Leukemia, Chronic Lymphocytic; Leukemia, Chronic Myelogenous; Leukemia, Hairy Cell; Lip and Oral Cavity Cancer; Liver Cancer; Lung Cancer, Non-Small Cell; Lung Cancer, Small Cell; Lymphoma, AIDS-Related; Lymphoma, Burkitt; Lymphoma, Cutaneous T-Cell; Lymphoma, Hodgkin; Lymphoma, Non-Hodgkin; Lymphoma, Primary Central Nervous System; Macroglobulinemia, Waldenstrom; Malignant Fibrous Histiocytoma of Bone and Osteosarcoma; Medulloblastoma; Melanoma; Melanoma, intraocular (Eye); Merkel Cell Carcinoma; Mesothelioma; Metastatic Squamous Neck Cancer with Occult Primary; Mouth Cancer; Multiple Endocrine Neoplasia Syndrome, (Childhood); Multiple Myeloma/Plasma Cell Neoplasm; Mycosis; Fungoides; Myelodysplastic Syndromes; Myelodysplastic/Myeloproliferative Diseases; Myelogenous Leukemia, Chronic; Myeloid Leukemia, Adult Acute; Myeloid Leukemia, Childhood Acute; Myeloma, Multiple; Myeloproliferative Disorders, Chronic; Nasal Cavity and Paranasal Sinus Cancer; Nasopharyngeal Cancer; Neuroblastoma; Non-Small Cell Lung Cancer; Oral Cancer; Oral Cavity Cancer; Oropharyngeal Cancer; Osteosarcoma and Malignant Fibrous Histiocytoma of Bone; Ovarian Cancer; Ovarian Epithelial Cancer; Ovarian Germ Cell Tumor; Ovarian Low Malignant Potential Tumor; Pancreatic Cancer; Pancreatic Cancer, Islet Cell Tumors; Papillomatosis; Parathyroid Cancer; Penile Cancer; Pharyngeal Cancer; Pheochromocytoma; Pineal Parenchymal Tumors of Intermediate Differentiation; Pineoblastoma and Supratentorial Primitive Neuroectodermal Tumors; Pituitary Tumor; Plasma Celt Neoplasm/Multiple Myeloma; Pleuropulmonary Blastoma; Primary Central Nervous System Lymphoma; Prostate Cancer; Rectal Cancer; Renal Cell (Kidney) Cancer; Renal Pelvis and Ureter, Transitional Cell Cancer; Respiratory Tract Carcinoma Involving the NUT Gene on Chromosome 15; Retinoblastoma; Rhabdomyosarcoma; Salivary Gland Cancer; Sarcoma, Ewing Family of Tumors; Sarcoma, Kaposi; Sarcoma, Soft Tissue; Sarcoma, Uterine; Sezary Syndrome; Skin Cancer (Nonmelanoma); Skin Cancer (Melanoma); Skin Carcinoma, Merkel Cell; Small Cell Lung Cancer; Small Intestine Cancer; Soft Tissue Sarcoma; Squamous Cell Carcinoma, Squamous Neck Cancer with Occult Primary, Metastatic; Stomach (Gastric) Cancer; Supratentorial Primitive Neuroectodermal Tumors; T-Cell Lymphoma, Cutaneous; Testicular Cancer; Throat Cancer; Thymoma and Thymic Carcinoma; Thyroid Cancer; Transitional Cell Cancer of the Renal Pelvis and Ureter; Trophoblastic Tumor, Gestational; Urethral Cancer; Uterine Cancer, Endometrial; Uterine Sarcoma; Vaginal Cancer; Vulvar Cancer; Waldenstrom Macroglobulinemia; and Wilms Tumor.

Activators

It will be understood by one skilled in the art, based upon the disclosure provided herein, that the invention relates to an activator of a biomarker of the invention. Activators of the invention encompass molecules that are associated with an increase in biomarker expression, including transcription, translation, or both or an increase in biomarker activity.

In various embodiments, the composition for treating a hematological neoplasia comprises an activator of PIGN. In one embodiment, the activator of the invention increases the amount of PIGN polypeptide, the amount of PIGN mRNA, the amount of PIGN activity, or a combination thereof.

In one embodiment, the composition for treating a hematological neoplasia comprises an activator of MAD1. In one embodiment, the activator of the invention increases the amount of MAD1 polypeptide, the amount of MAD1 mRNA, the amount of MAD1 activity, or a combination thereof.

In one embodiment, the present invention relates to methods for prevention and treatment of a hematological neoplasia or disorder by administration of an activator of the invention. In one embodiment, the activator of the invention increases the amount of PIGN polypeptide, the amount of PIGN mRNA, the amount of PIGN activity, or a combination thereof. In one embodiment, the activator of the invention increases the amount of MAD1 polypeptide, the amount of MAD1 mRNA, the amount of MAD1 activity, or a combination thereof.

Activation of a biomarker can be assessed using a wide variety of methods, including those disclosed herein, as well as methods well-known in the art or to be developed in the future. That is, the skilled artisan would appreciate, based upon the disclosure provided herein, that increasing the level or activity of a biomarker can be readily assessed using methods that assess the level of a nucleic acid encoding the biomarker (e.g., mRNA) and/or the level of polypeptide of the biomarker in a biological sample obtained from a subject.

An activator can include, but should not be construed as being limited to, a chemical compound, a protein, a peptidomimetic, an antibody, a nucleic acid molecule. Additionally, an activator encompasses a chemically modified compound, and derivatives, as are well known to one of skill in the chemical arts.

In one embodiment, a PIGN activator encompasses a chemical compound that increases the level, enzymatic activity, or the like of PIGN. In some embodiments, the enzymatic activity is GPI-anchor protein biosynthesis.

In one embodiment, a MAD1 activator encompasses a chemical compound that increases the level, enzymatic activity, or the like of MAD1. In some embodiments, the enzymatic activity is preventing interaction of MAX with MYC.

One of skill in the art would appreciate that an activator includes such activators as discovered in the future, as can be identified by well-known criteria in the art of pharmacology. Therefore, the present invention is not limited in any way to any particular activator as exemplified or disclosed herein; rather, the invention encompasses those activators that would be understood by the skilled artisan to be useful as are known in the art and as are discovered in the future.

Further methods of identifying and producing an activator are well known to those of ordinary skill in the art, including, but not limited, obtaining an activator from a naturally occurring source. Alternatively, an activator can be synthesized chemically. Further, the skilled artisan would appreciate, based upon the teachings provided herein, that an activator can be obtained from a recombinant organism. Compositions and methods for chemically synthesizing activators and for obtaining them from natural sources are well known in the art and are described in the art.

One of skill in the art will appreciate that an activator can be administered as a small molecule chemical, a protein, a nucleic acid construct encoding a protein, or combinations thereof. Numerous vectors and other compositions and methods are well known for administering a protein or a nucleic acid construct encoding a protein to cells or tissues. Therefore, in one embodiment, the invention includes a method of administering a protein or a nucleic acid encoding a protein that is an activator of PIGN. In one embodiment, the invention includes a method of administering a protein or a nucleic acid encoding a protein that is an activator of MAD1.

Administration and Formulation

In one embodiment, a method of treating a hematological neoplasia or disorder encompasses administering to a subject a polypeptide, a recombinant polypeptide, an active polypeptide fragment, or an activator of a biomarker of the invention as a preventative measure against a hematological neoplasia or disorder. As more fully discussed elsewhere herein, methods of increasing the level or activity of a biomarker encompass a wide plethora of techniques for increasing not only biomarker activity, but also for increasing expression of a nucleic acid encoding the biomarker. Additionally, as disclosed elsewhere herein, one skilled in the art would understand, once armed with the teaching provided herein, that the present invention encompasses a method of preventing a wide variety of diseases where increased expression and/or activity of a biomarker of the invention mediates, treats or prevents the disease. Further, the invention encompasses treatment or prevention of such diseases discovered in the future.

In one embodiment, the invention encompasses administration of a PIGN polypeptide, a recombinant PIGN polypeptide, an active PIGN polypeptide fragment, a PIGN activator, or an inhibitor of a negative regulator of PIGN (e.g., an inhibitor of a PIGN inhibitor) to a subject in need thereof. In one embodiment, the invention encompasses administration of a MAD1 polypeptide, a recombinant MAD1 polypeptide, an active MAD1 polypeptide fragment, a MAD1 activator, or an inhibitor of a negative regulator of MAD1 to a subject in need thereof. To practice the methods of the invention; the skilled artisan would understand how to formulate and administer the appropriate activator for administration to a subject. However, the present invention is not limited to any particular method of administration or treatment regimen.

Inhibitors

In one embodiment, the invention relates to inhibitors of a gene or gene product that PIGN interacts with. In one embodiment, the invention relates to inhibitors of PKR.

One of skill in the art will realize that diminishing the amount or activity of a molecule that itself diminishes the amount or activity of PIGN can serve to increase the amount or activity of PIGN. Similarly, diminishing the amount or activity of a molecule that itself diminishes the amount or activity of MAD1 can serve to increase the amount or activity of MAD1. Therefore, an inhibitor of a negative regulator of a biomarker of the invention is encompassed as an activator of the invention.

In one embodiment, an inhibitor of the invention decreases level of a gene or gene product. It will be understood by one skilled in the art that a decrease in the level of a gene encompasses the decrease in the expression, including transcription, translation, or both. The skilled artisan will also appreciate that a decrease in the level of gene or gene product includes a decrease in the activity of the gene or gene product.

In one embodiment, the inhibitor of the invention decreases the amount of polypeptide, the amount of mRNA, the amount of activity, or a combination thereof of a gene or gene product PIGN interacts with. In one embodiment, the inhibitor of the invention decreases the amount of polypeptide, the amount of mRNA, the amount of activity, or a combination thereof of PKR.

In one embodiment, a gene or gene product PIGN interacts with is a regulator of PIGN. In one embodiment, the inhibitor of the invention decreases the amount of polypeptide, the amount of mRNA, the amount of activity, or a combination thereof of a gene or gene product MAD1 interacts with. In one embodiment, the inhibitor of the invention decreases the amount of polypeptide, the amount of mRNA, the amount of activity, or a combination thereof of MAX.

In one embodiment, the inhibitor is selected from the group consisting of a small interfering RNA (siRNA), a microRNA, an antisense nucleic acid, a ribozyme, an expression vector encoding a transdominant negative mutant, an intracellular antibody, a peptide and a small molecule.

In one embodiment, antisense oligonucleotides are useful as an inhibitor of the invention. Antisense oligonucleotides are DNA or RNA molecules that are complementary to some portion of an mRNA molecule. When present in a cell, antisense oligonucleotides hybridize to an existing mRNA molecule and inhibit translation into a gene product. Inhibiting the expression of a gene using an antisense oligonucleotide is well known in the art (Marcus-Sekura, 1988, Anal. Biochem. 172:289), as are methods of expressing an antisense oligonucleotide in a cell (Inoue, U.S. Pat. No. 5,190,931).

Contemplated in the present invention are antisense oligonucleotides that are synthesized and provided to the cell by way of methods well known to those of ordinary skill in the art. As an example, an antisense oligonucleotide can be synthesized to be between about 10 and about 100, more preferably between about 15 and about 50 nucleotides long. The synthesis of nucleic acid molecules is well known in the art, as is the synthesis of modified antisense oligonucleotides to improve biological activity in comparison to unmodified antisense oligonucleotides (Tullis, 1991, U.S. Pat. No. 5,023,243).

The expression of a gene may be inhibited by the hybridization of an antisense oligonucleotide to a promoter or other regulatory element of a gene, thereby affecting the transcription of the gene. Methods for the identification of a promoter or other regulatory element that interacts with a gene of interest are well known in the art, and include such methods as the yeast two hybrid system (Bartel and Fields, eds., In: The Yeast Two Hybrid System, Oxford University Press, Cary, N.C.).

In one embodiment, siRNA is used as an inhibitor of the invention. RNA interference (RNAi) is a phenomenon in which the introduction of double-stranded RNA (dsRNA) into a diverse range of organisms and cell types causes degradation of the complementary mRNA. In the cell, long dsRNAs are cleaved into short 21-25 nucleotide small interfering RNAs, or siRNAs, by a ribonuclease known as Dicer. The siRNAs subsequently assemble with protein components into an RNA-induced silencing complex (RISC), unwinding in the process. Activated RISC then binds to complementary transcript by base pairing interactions between the siRNA antisense strand and the mRNA. The bound mRNA is cleaved and sequence specific degradation of mRNA results in gene silencing. See, for example, U.S. Pat. No. 6,506,559; Fire et al., 1998, Nature 391(19): 306-311; Timmons et al., 1998, Nature 395:854; Montgomery et al., 1998, TIG 14 (7):255-258; David R. Engelke, Ed., RNA Interference (RNAi) Nuts & Bolts of RNAi Technology, DNA Press, Eagleville, P A (2003); and Gregory J. Hannon, Ed., RNAi A Guide to Gene Silencing, Cold Spring Harbor Laboratory Press, Cold Spring Harbor, N.Y. (2003). Soutschek et al. (Soutschek et al., 2004, Nature 432:173-178) describe a chemical modification to siRNAs that aids in intravenous systemic delivery. Optimizing siRNAs involves consideration of overall G/C content, C/T content at the termini, Tm and the nucleotide content of the 3' overhang. See, for instance, Schwartz et al., 2003, Cell, 115:199-208 and Khvorova et al., 2003, Cell 115:209-216. Therefore, the present invention also includes methods of decreasing levels of a regulator of PIGN at the protein level using RNAi technology.

Alternatively, an inhibitor of the invention may be a ribozyme. Using ribozymes for inhibiting gene expression is well known to those of skill in the art (see, e.g., Cech et al., 1992, J. Biol. Chem. 267:17479; Hampel et al., 1989, Biochemistry 28: 4929; Altman et al., U.S. Pat. No. 5,168,053). Ribozymes are catalytic RNA molecules with the ability to cleave other single-stranded RNA molecules. Ribozymes are known to be sequence specific, and can therefore be modified to recognize a specific nucleotide sequence (Cech, 1988, J. Amer. Med. Assn. 260:3030), allowing the selective cleavage of specific mRNA molecules. Given the nucleotide sequence of the molecule, one of ordinary skill in the art could synthesize an antisense oligonucleotide or ribozyme without undue experimentation, provided with the disclosure and references incorporated herein.

In other related aspects, the invention includes an isolated nucleic acid encoding an inhibitor, wherein an inhibitor such as an siRNA or antisense oligonucleotide, inhibits a regulator of a biomarker of the invention, a derivative thereof, a regulator thereof, or a downstream effector, operably linked to a nucleic acid comprising a promoter/regulatory sequence such that the nucleic acid is preferably capable of directing expression of the protein encoded by the nucleic acid. Thus, the invention encompasses expression vectors and methods for the introduction of exogenous DNA into cells with concomitant expression of the exogenous DNA in the cells such as those described, for example, in Sambrook et al. (2012, Molecular Cloning: A Laboratory Manual, Cold Spring Harbor Laboratory, New York) and as described elsewhere herein. In another aspect of the invention, a regulator of a biomarker of the invention, can be inhibited by way of inactivating and/or sequestering the regulator. As such, inhibiting the effects of a regulator of a biomarker of the invention can be accomplished by using a transdominant negative mutant. In one embodiment, the inhibitor is a protein and/or compound having the desirable property of interacting with a binding partner of a regulator of a biomarker of the invention and thereby competing with the corresponding protein. In another embodiment, the antagonist is a protein and/or compound having the desirable property of interacting with a regulator of a biomarker of the invention and thereby sequestering the regulator.

In one embodiment, the invention includes a vector comprising a siRNA or antisense oligonucleotide. In one embodiment, the siRNA or antisense oligonucleotide is capable of inhibiting the expression of a regulator of a biomarker of the invention. The incorporation of a desired polynucleotide into a vector and the choice of vectors is well-known in the art as described in, for example, Sambrook et al., supra. The siRNA or antisense polynucleotide can be cloned into a number of types of vectors for expression of the siRNA or antisense oligonucleotide.

In order to assess the expression of the siRNA or antisense oligonucleotide, the expression vector to be introduced into a cell can also contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neomycin resistance and the like.

In one embodiment of the invention, an antisense nucleic acid sequence which is expressed by a plasmid vector is used to inhibit one or more of PKR, a regulator of PIGN and MAX. The antisense expressing vector is used to transfect a mammalian cell or the mammal itself, thereby causing reduced endogenous expression of one or more of PKR, a regulator of PIGN and MAX.

When the inhibitor of the invention is a small molecule, a small molecule antagonist may be obtained using standard methods known to the skilled artisan. Such methods include chemical organic synthesis or biological means. Biological means include purification from a biological source, recombinant synthesis and in vitro translation systems, using methods well known in the art.

Combinatorial libraries of molecularly diverse chemical compounds potentially useful in treating a variety of diseases and conditions are well known in the art as are method of making the libraries. The method may use a variety of techniques well-known to the skilled artisan including solid phase synthesis, solution methods, parallel synthesis of single compounds, synthesis of chemical mixtures, rigid core structures, flexible linear sequences, deconvolution strategies, tagging techniques, and generating unbiased molecular landscapes for lead discovery vs. biased structures for lead development.

In a general method for small library synthesis, an activated core molecule is condensed with a number of building blocks, resulting in a combinatorial library of covalently linked, core-building block ensembles. The shape and rigidity of the core determines the orientation of the building blocks in shape space. The libraries can be biased by changing the core, linkage, or building blocks to target a characterized biological structure ("focused libraries") or synthesized with less structural bias using flexible cores.

As will be understood by one skilled in the art, any antibody that can recognize and bind to a negative regulator of a biomarker of the invention is useful as an inhibitor in the present invention. Methods of making and using antibodies are well known in the art. For example, polyclonal antibodies useful in the present invention are generated by immunizing rabbits according to standard immunological techniques well-known in the art (see, e.g., Harlow et al., 1988, In: Antibodies, A Laboratory Manual, Cold Spring Harbor, N.Y.). Monoclonal antibodies directed against full length or peptide fragments of a protein or peptide may be prepared using any well-known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (1992, Critical Rev. Immunol. 12:125-168), and the references cited therein. Further, the antibody of the invention may be "humanized" using the technology described in, for example, Wright et al., and in the references cited therein, and in Gu et al. (1997, Thrombosis and Hematocyst 77:755-759), and other methods of humanizing antibodies well-known in the art or to be developed.

Pharmaceutical Administration

In certain embodiments, treatment comprises administering a disease-modulating drug to a subject. The drug can be a therapeutic or prophylactic used in subjects diagnosed or identified with a disease or at risk of having the disease. In certain embodiments, modifying therapy refers to altering the duration, frequency or intensity of therapy, for example, altering dosage levels.

In various embodiments, effecting a therapy comprises causing a subject to or communicating to a subject the need to make a change in lifestyle, for example, increasing exercise, changing diet, reducing or eliminating smoking and so on. The therapy can also include surgery.

Measurement of biomarker levels allow for the course of treatment of a disease to be monitored. The effectiveness of a treatment regimen for a disease can be monitored by detecting one or more biomarkers in an effective amount from samples obtained from a subject over time and comparing the amount of biomarkers detected. For example, a first sample can be obtained prior to the subject receiving treatment and one or more subsequent samples are taken after or during treatment of the subject. Changes in biomarker levels across the samples may provide an indication as to the effectiveness of the therapy.

To identify therapeutics or drugs that are appropriate for a specific subject, a test sample from the subject can also be exposed to a therapeutic agent or a drug, and the level of one or more biomarkers can be determined. Biomarker levels can be compared to a sample derived from the subject before and after treatment or exposure to a therapeutic agent or a drug, or can be compared to samples derived from one or more subjects who have shown improvements relative to a disease as a result of such treatment or exposure. Thus, in one aspect, the invention provides a method of assessing the efficacy of a therapy with respect to a subject comprising taking a first measurement of a biomarker panel in a first sample from the subject; effecting the therapy with respect to the subject; taking a second measurement of the biomarker panel in a second sample from the subject and comparing the first and second measurements to assess the efficacy of the therapy.

Additionally, therapeutic or prophylactic agents suitable for administration to a particular subject can be identified by detecting a biomarker (which may be two or more) in an effective amount from a sample obtained from a subject and exposing the subject-derived sample to a test compound that determines the amount of the biomarker(s) in the subject-derived sample. Accordingly, treatments or therapeutic regimens for use in subjects having a disease or subjects at risk for developing a disease can be selected based on the amounts of biomarkers in samples obtained from the subjects and compared to a reference value. Two or more treatments or therapeutic regimens can be evaluated in parallel to determine which treatment or therapeutic regimen would be the most efficacious for use in a subject to delay onset, or slow progression of a disease. In various embodiments, a recommendation is made on whether to initiate or continue treatment of a disease.

In various exemplary embodiments, effecting a therapy comprises administering a gene therapy or a disease-modulating drug to the subject. The subject may be treated with one or more gene therapies or disease-modulating drugs until altered levels of the measured biomarkers return to a baseline value measured in a population not suffering from the disease, experiencing a less severe stage or form of a disease or showing improvements in disease biomarkers as a result of treatment with a disease-modulating drug. Additionally, improvements related to a changed level of a biomarker or clinical parameter may be the result of treatment with a gene therapy or disease-modulating drug.

A number of compounds such as a disease-modulating drug may be used to treat a subject and to monitor progress using the methods of the invention. In certain embodiments, the disease-modulating drug comprises Cytarabine, Anthracycline, Idarubicin, Daunorubicin, Cladribine, a nucleoside analog, an alkylating agent, a farnesyl transferase inhibitor, a DNMT1 inhibitor, a proteasome inhibitor, a topoisomerase inhibitor, a chemotherapeutic, all-trans retinoic acid (ATRA), arsenic trioxide, an epigenetic modulator, a HDAC inhibitor, a BTK modulator, a PI3K pathway modulator, a mTOR inhibitor, a PD-1/L inhibitor, a Polo-like kinase inhibitor, an Aurora kinase inhibitor, an immunotherapeutic, a monoclonal antibody, a drug for treatment of AML or a drug for treatment of MDS. In one embodiment, a disease-modulating drug may be one of Hycamtin, Revlimid, Epogen, Aranesp, Dacogen or Vidaza.

The beneficial effects of these and other drugs can be visualized by assessment of clinical and laboratory biomarkers.

Any drug or combination of drugs disclosed herein may be administered to a subject to treat a disease. The drugs herein can be formulated in any number of ways, often according to various known formulations in the art or as disclosed or referenced herein.

In various embodiments, any drug or combination of drugs disclosed herein is not administered to a subject to treat a disease. In these embodiments, the practitioner may refrain from administering the drug or combination of drugs, may recommend that the subject not be administered the drug or combination of drugs or may prevent the subject from being administered the drug or combination of drugs.

In various embodiments, one or more additional drugs may be optionally administered in addition to those that are recommended or have been administered. An additional drug will typically not be any drug that is not recommended or that should be avoided. In certain embodiments, one or more additional drugs comprise one or more of Cytarabine, Anthracycline, Idarubicin, Daunorubicin, Cladribine, a nucleoside analog, an alkylating agent, a farnesyl transferase inhibitor, a DNMT1 inhibitor, a proteasome inhibitor, a topoisomerase inhibitor, a chemotherapeutic, all-trans retinoic acid (ATRA), arsenic trioxide, an epigenetic modulator, a HDAC inhibitor, a BTK modulator, a PI3K pathway modulator, a mTOR inhibitor, a PD-1/L inhibitor, a Polo-like kinase inhibitor, an Aurora kinase inhibitor, an immunotherapeutic, a monoclonal antibody, a drug for treatment of AML or a drug for treatment of MDS. In one embodiment, the combination of drugs to be administered is a cytarabine-anthracycline combination.

In various embodiments, a practitioner may provide counseling to a patient and/or refer a patient for a clinical trial based on the diagnosis of the invention. In one embodiment, a practitioner may recommend monitoring of a patient for development of a hematological neoplasia or progression of MDS to AML based on the diagnosis of the invention.

In one embodiment, the invention is used in combination with a prognostic scoring system. Prognostic scoring systems that are appropriate for use with the invention include but are not limited to International Prognostic Scoring System (IPSS), revised as the IPSS-R; the WHO Prognostic Scoring System (WPSS); and the MD Anderson Cancer Center Prognostic Scoring System.

Gene Therapy Administration

In one embodiment, a recommended treatment may include gene therapy. In one embodiment, a therapeutic agent comprising a nucleic acid molecule encoding a biomarker of the invention is provided to a patient. In one embodiment, a nucleic acid molecule encoding a biomarker protein is a vector.

One skilled in the art recognizes that different methods of delivery may be utilized to administer a vector into a cell. Examples include: (1) methods utilizing physical means, such as electroporation (electricity), a gene gun (physical force) or applying large volumes of a liquid (pressure); and (2) methods wherein said vector is complexed to another entity, such as a liposome, aggregated protein or transporter molecule.

Furthermore, the actual dose and schedule can vary depending on whether the compositions are administered in combination with other pharmaceutical compositions, or depending on inter-individual differences in pharmacokinetics, drug disposition, and metabolism. Similarly, amounts can vary in in vitro applications depending on the particular cell line utilized (e.g., based on the number of vector receptors present on the cell surface, or the ability of the particular vector employed for gene transfer to replicate in that cell line). Furthermore, the amount of vector to be added per cell will likely vary with the length and stability of the therapeutic gene inserted in the vector, as well as also the nature of the sequence, and is particularly a parameter which needs to be determined empirically, and can be altered due to factors not inherent to the methods of the present invention (for instance, the cost associated with synthesis). One skilled in the art can easily make any necessary adjustments in accordance with the exigencies of the particular situation.

Cells containing the therapeutic agent may also contain a suicide gene i.e., a gene which encodes a product that can be used to destroy the cell. In many gene therapy situations, it is desirable to be able to express a gene for therapeutic purposes in a host cell, but also to have the capacity to destroy the host cell at will. The therapeutic agent can be linked to a suicide gene, whose expression is not activated in the absence of an activator compound. When death of the cell in which both the agent and the suicide gene have been introduced is desired, the activator compound is administered to the cell thereby activating expression of the suicide gene and killing the cell. Examples of suicide gene/prodrug combinations which may be used are herpes simplex virus-thymidine kinase (HSV-tk) and ganciclovir, acyclovir; oxidoreductase and cycloheximide; cytosine deaminase and 5-fluorocytosine; thymidine kinase thymidilate kinase (Tdk::Tmk) and AZT; and deoxycytidine kinase and cytosine arabinoside.

In one embodiment, an activator of the invention can be administered to prevent or treat a hematological neoplasia or disorder. Further, an activator of the invention can be administered alone or in combination with another therapy to effect a therapeutic result. In one embodiment, an activator of PIGN is administered in combination with an activator of MAD1. In one embodiment, an activator of PIGN can be administered simultaneously with, before, and/or after an activator of MAD1.

Pharmaceutical Compositions

The present invention includes pharmaceutical compositions comprising one or more modulators of PIGN and/or the genes or gene products PIGN interacts with. In one embodiment, the present invention includes pharmaceutical compositions comprising one or more modulators of MAD1 and/or the genes or gene products MAD1 interacts with. The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the description of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions that are useful in the methods of the invention may be prepared, packaged, or sold in formulations suitable for ophthalmic, oral, rectal, vaginal, parenteral, topical, pulmonary, intranasal, buccal, intratumoral, epidural, intracerebral, intracerebroventricular, or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents.

Controlled- or sustained-release formulations of a pharmaceutical composition of the invention may be made using conventional technology. Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi dose containers containing a preservative.

Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non toxic parenterally acceptable diluent or solvent, such as water or 1,3 butane diol, for example. Other acceptable diluents and solvents include, but are not limited to, Ringer's solution, isotonic sodium chloride solution, and fixed oils such as synthetic mono- or di-glycerides.

Other parenterally-administrable formulations that are useful include those that comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present

Example 1: PIGN Gene Expression Aberration is Associated with Genomic Instability and Leukemia Progression in a Subgroup of Acute Myelogenous Leukemia with Myelodysplastic Feature Previous studies have proposed an increased frequency of glycosylphosphatidylinositol-anchored protein (GPI-AP) deficiency as a marker of genomic instability to predict the risk of leukemic transformation (Chen et al., Cancer Res. 2001, 61:654-658; Araten et al., Cancer Res. 2005, 65:8111-8117; Peruzzi et al., Mutat. Res.-Rev. Mutat. Res. 2010, 705:3-10; Pu et al., J Clin Oncol. 2013, 1-2). Recently, a GPI-anchor biosynthesis class N gene (PIGN), which is located at the 18q21.33 locus, was identified as a CIN suppressor in a colorectal cancer cell model (Burrell et al., Nature 2013, 494:492-496). The PIGN gene encodes a phosphoethanolamine (EtNP) transferase involved in the terminal steps of GPI-AP anchor biosynthesis (Hong et al., J Biol Chem, 1999, 274:35099-35106; Yada et al., J Biol Chem. 2001, 276:13579-13586). In that study, Burrell et al. demonstrated that PIGN gene silencing by either chromosomal 18q deletion or transfection of short interfering RNAs (siRNAs) resulted in DNA replication stress, structural chromosome abnormalities, and chromosome missegregation. Furthermore, PIGN gene silencing and aneuploidy were observed during the process of adenoma-carcinoma transition.

However, no literature has yet addressed the role of the PIGN gene in hematological malignancy formation and progression. Furthermore, there is no report on concurrent gene expression alterations involving both PIGN and TP53 during AML progression. In this study, 18 patients with either high risk MDS or AML associated with myelodysplastic features were screened, and a PIGN gene expression aberration (increased transcription activity but diminished protein production) was identified. Further, two AML patients who harbored both PIGN gene expression aberration and TP53 gene deletion were studied in detail. This study indicates that PIGN gene expression aberration may aggravates genomic instability and cause AML progression in a subgroup of patients with myelodysplastic features.

The Methods are Now Described

Patient Selection

This study was approved by the Institutional Review Board of the Pennsylvania State University College of Medicine. All patients in this study were evaluated by the authors at either outpatient clinic or inpatient wards between July 2012 and December 2015. MDS and AML were diagnosed as per WHO criteria (Swerdlow et al., IARC Press, 2008). The bone marrow aspiration and biopsy samples were evaluated by hematopathologists at the university medical center. The venous peripheral blood and bone marrow aspiration for experiment use were drawn into heparin-containing tubes after informed consent.

Cell Lines

KG1, KG1a and K562 cells (ATCC) were cultured in IMDM supplemented with 20% FBS. MDS92 and MDS-L cells were cultured in RPMI-1640 supplemented with 10% FBS, 50 ng/ml IL-3 (Miltenyi Biotec) and 50 µM 2-mercaptoethanol (Fisher Scientific). HEK293 and HEK293 PIGN CRISPR/Cas9 knockout cells were cultured in DMEM supplemented with 10% FBS. Cell lines were passaged on average every 3-4 days. CD34+ mononuclear cells were cultured in DMEM/F12 supplemented with 10% FBS, 50 µM 2-mercaptoethanol, Glutamax (Life Technologies), MEM non-essential amino acids (Life Technologies) and StemMACS HSC expansion cocktail (Miltenyi Biotec). All cells were cultured at 37° C. under 5% CO2 conditions.

Isolation of Mononuclear and CD34+ Cells

Mononuclear cells were isolated from peripheral blood or bone marrow aspirates using Ficoll-Paque PLUS (GE Healthcare Life Sciences) according to the manufacturer's protocol. CD34+ cells where applicable, were isolated from the mononuclear cells via MACS® Technology (Miltenyi Biotec) with the human CD34 MicroBead Kit (Miltenyi Biotec) in accordance with the manufacturer's protocol.

Leukemic Blast Sorting

Leukemic blast sorting was conducted under BSL-2 conditions with a 16-color BD FACSAria SORP high speed cell sorter (Becton Dickinson) in the Institutional Flow Cytometry Core Facility. CD34+ cells that expressed HLA-DR, CD13, CD117 and CD45 were sorted as leukemic cells. However, CD34+ cells that did not express HLA-DR, CD13, CD117 and CD45 were sorted as non-leukemic cells.

Selection of Proaerolysin-Resistant CFCs and GPI-AP Deficiency Frequency Analysis Bone marrow CD34+ mononuclear cells were processed for growth of colony forming units (CFCs). The bone marrow CD34+ mononuclear cells were cultured in 1 ml Methcult complete medium w/o Epo (Miltenyi Biotec) with or without 1 nM of proaerolysin. The selection of proaerolysin-resistant colony forming cells (CFCs) was conducted as earlier described with some modifications (Pu et al., Haematologica, 2012, 97:1225-1233). The frequency of GPI-AP deficiency was calculated as described (Pu et al., Haematologica, 2012, 97:1225-1233).

PIGN Knockdown Studies

PIGN knockdown experiments were conducted using the Nucleofector™ II Device (Amaxa) in conjunction with the Cell line Nucleofector® Kit V reagent kit (Amaxa) according the manufacturer's recommended protocols for the various cell lines. The cells were transfected with 100 nM siGENOME™ siRNA Human PIGN, D-012463-01 (Dharmacon) or 100 nM siGENOME™ Control siRNA Non-targeting siRNA #2, D-001210-02-05 (Dharmacon) and incubated for 24-72 hours.

PIGN Gene Expression Via qRT-PCR

Total RNA was isolated from $1\times10^6$ leukemic sorted cells using the RNeasy Mini Kit (Qiagen) according to the manufacturer's instructions. Total RNA (20 ng/µl) was reverse transcribed using the High Capacity cDNA reverse transcription kit (Life Technologies) on the Mastercycler® nexus (Eppendorf). Real time qPCR step was conducted on the StepOnePlus™ real time PCR System (ABI systems) using the PIGN gene expression assay Hs00202443_m1 (Life Technologies) and 18S Hs99999901_s1 (Life Technologies) gene expression as internal reference. The PIGN gene expression assay was designed to have the best coverage for the reported transcript variants of the PIGN gene and targets the exon boundary between exon 5 and exon 6. H2AX, Baxa, DR5, SIRT1, SAE2 and p21 primers as well as GAPDH and HPRT internal control primers (Integrated DNA Technologies) were used with Power SYBR® Green PCR Master Mix (Life Technologies). The selected gene expression profile in the leukemic phase and non-leukemic phase were conducted via reverse transcription-qPCR (RT-qPCR) as described (Hasanali et al., Sci. Transl. Med. 2015, 7:293ra102). For all experiments, samples were run in triplicates and expression data was normalized to PIGN gene expression in normal healthy control peripheral blood mononuclear cells (PBMCs) or CD34+ mononuclear cells. Gene expression was calculated using the delta delta Ct method.

Western Blot Analyses

Cells were lysed in RIPA lysis buffer (Sigma-Aldrich) with protease and phosphatase inhibitor cocktails (Sigma). Protein concentration was determined by Bradford Assay (Life Technologies). Total protein lysate (15-40 µg) was separated in a NuPAGE™ 4-12% Bis-Tris Gel (Life Technologies) and transferred to Immun-Blot® PVDF Membrane (Bio-Rad). The blots were incubated overnight with anti-PIGN antibodies (HPA039922, Atlas Antibodies; and L-20: sc-85103, Santa Cruz); anti-MAD1 antibodies (Clone BB3-8, MABE867, Millipore), anti-Histone H2A.X (D17A3, Cell Signaling Technology) anti-phospho-Histone H2A.X ser139 (S139, Cell Signaling Technology) and HA-Tag (C29F4, Cell Signaling Technology) in TBS-T with 5% Non-Fat Dry Milk. The blots were subsequently probed with a horse radish peroxidase conjugated goat anti-rabbit IgG (AP132P, Millipore) or goat anti-mouse IgG antibody (AP124P, Millipore) and developed by ECL Prime (Amersham). Mouse beta-actin (C-4, sc-47778, Santa Cruz Biotechnology) was used as loading control.

PIGN Sequence Analyses

RT-PCR was conducted with Invitrogen SuperScript One step RT-PCR with Platinum Taq kit (Invitrogen) using RNA isolated from the leukemic-sorted cells. PCR products were sub-cloned into PCR2.1 TOPO vector (Invitrogen) and individual clones were selected on Amp+X-gal blue/white selection plates. The plasmids were isolated using the GeneJET Plasmid miniprep Kit (Life Technologies). M13 universal primers (Invitrogen) were used for screening the PCR insert size and sequencing was conducted at MCLAB Molecular Cloning Laboratories, South San Francisco, Calif. Sequencing data was analyzed with reference to PIGN NCBI Reference Sequences: NG_033144.1 and NM_012327.5 using the CLC Sequence Viewer Version 7.6 (QIAGEN Aarhus A/S) in conjunction with manual inspection. Impact of aberrations on protein coding was conducted using the Sequence Manipulation Suite with reference to PIGN protein sequence NP_036459.1.

PIGN Knockdown and CRISPR/Cas9 Knockout Studies

RNAi-mediated PIGN knockdown experiments were conducted using the Nucleofector™ II Device (Amaxa) in conjunction with the Cell line Nucleofector™ Kit V reagent kit (Amaxa) according to the manufacturer's recommended protocols for the various cell lines. The cells were transfected with 100 nM siGENOME™ siRNA Human PIGN, (D-012463-01, Dharmacon) or 100 nM siGENOME™ Control siRNA Non-targeting siRNA #2, (D-001210-02-05, Dharmacon) and incubated for 24-72 hours. CRISPR/Cas9 experiments were conducted according to a modified LentiCRISPRv2 (Addgene plasmid #49535) protocol (Sanjana et al., Nat. Methods. 2014, 11:783-784). The gRNA (AAACGGTCATGTAGCTCTGATAGC) (SEQ ID NO:1) we employed targets PIGN at exon 4 and results in a frameshift (Ohba et al., Neurogenetics. 2014, 15:85-92). The Lentiviral transduced CD34+ mononuclear cells were harvested for downstream applications 9 days post-infection.

HA Tag IP/Co-IP Analyses

PIGN-HA IP/Co-IP experiments were conducted by transient transfection of CRISPR/Cas9 PIGN knockout HEK293 cells with the SRα promoter-driven expression vector pME Puro 3HA hPIGN or the empty vector without PIGN cDNA cloned (Ohba et al., Neurogenetics. 2014, 15:85-92). The cells were transfected with 5 µg of the vector using the Lipofectamine 3000 transfection reagent (Life Technologies) according to the manufacturer's protocol. Protein samples were obtained 48 hours post transfection and 250 µg protein was used with the HA Tag IP/Co-IP Kit according to the manufacturers protocol. The eluates and 10% of the input lysates were used for Western blot analyses.

TP53 Sequence Analyses

One microgram of DNA isolated from non-leukemic cells and leukemic cells was amplified using primers covering exon 2-11 of the TP53 gene including intron/exon boundaries according to instructions in the IARC database. Seven PCR reactions per sample (non-leukemic and leukemic) were spin column purified and sequenced using the 3130XL Genetic Analyzer (ABI systems) with the same primers in both reverse and forward directions. FinchTV version 1.4.0 and nucleotide BLAST were used for sequence analyses (Altschul et al., J. Mol. Biol. 1990, 215:403-410). Sequencing results were aligned to the TP53 GenBank sequence NC_000017.9 and sequence alterations were partly identified via manual inspection. Sequence alterations were aligned with the coding sequence of the TP53 protein and the impact on protein was determined using the IARC database and Sorting Intolerant From Tolerant (SIFT).

Cell Cycle Block/Synchronization

Cell synchronization at the Go/G1, S and G2/M phases were conducted based on modified protocols (Jackman and O'Connor, Curr. Protoc. Cell Biol. 2001; Chapter 8: Unit 8.3). Cell synchrony was monitored using propidium iodide-stained cells with the FACS Calibur flow cytometer (BD Biosciences). Protein lysates were obtained and used for Western blot analyses as earlier described.

Immunofluorescence and Confocal Microscopy

For missegregation and co-localization analyses, cells were blocked in early S-phase via the double thymidine treatment and released for 6-8 hours into the mitotic phase. Adherent cells were cultured on chambered slides. Cytospin was used to fix suspension cells on to the slides. Cells were fixed in 4% paraformaldehyde in PBS and permeabilized in −20° C. 100% methanol. The slides were blocked in 2.5% normal goat serum diluted in PBS. For all wash steps, the cells were washed three times for 5 mins each in PBS. The cells were treated at 4° C. overnight with primary antibodies: Human anti-centromere (kinetochore) (15-234, Antibodies Incorporated), PIGN (HPA039922, Atlas Antibodies) and MAD1 (Clone BB3-8, MABE867, Millipore) followed by washing and treatment for 2 hours at room temperature in the dark with secondary antibodies (1:1000): Alexa Fluor® 647 goat anti-human IgG (H+L) (A21445, Life Technologies), Goat anti-rabbit IgG, Dylight® 488 Conjugated Highly cross-adsorbed (35553, Life Technologies) and Goat anti-mouse IgG, Dylight™ 633 Conjugated (35513, Life Technologies) respectively. Antibodies were diluted in 1% normal goat serum diluted in PBS. The slides were partially dried in the dark and mounted in Vectashield Hard Set™ mounting medium with DAPI (H-1500, Vector Laboratories). Images were acquired using the Leica SP8 Inverted confocal microscope at the Microscopy Imaging Facility at Penn State College of Medicine. Three-dimensional image stacks were acquired in 0.15-µm steps using a ×40 1.4 N.A oil immersion objective. Deconvolution and analyses of image stacks were performed using the Huygens workstation (Scientific Volume Imaging B.V.) and the Imaris Microscopy Image Analysis software (Bitplane AG).

Bioinformatics Analyses and Statistical Analyses

The GENE-E matrix visualization and analysis platform was used to generate a heat map of the CIN-70 signature of the CD34+ cells of 55 MDS patients and 11 healthy controls utilizing data generated on the Affymetrix GeneChip U133

Plus2.0 platform from the study GSE4619 (Carter et al., Nat Genet. 2006, 38:1043-1048; Pellagatti et al., Blood, 2006, 108:337-345).

The randomForest v4.6-12 R package with default parameters was used in a randomForest Analysis to classify patients based on MDS risk stratification.

RNA-seq Analysis study was conducted on raw RNA-seq files for the dbGAP study phs001027.v1. The RNA-seq reads were aligned to the most recent reference genomes (hg38) using Tophat (v2.0.9) (Trapnell et al., Bioinformatics 2009, 25:1105-1111) by allowing up to 2 mismatches. The junction files data analyses were loaded on to IGV (Integrated Genome Viewer) to survey intronic frame shift in PIGN genes.

GraphPad Prism 5 software and Microsoft Excel 2010 were used for statistical analyses. Two-tailed Student's t-tests and One-way ANOVA followed by Tukey's post hoc tests were used for comparisons. p-values ≤0.05 were considered statistically significant.

The Experimental Results are Now Described

PIGN Gene Expression Profile Links to Genomic Stability, Especially MDS Progression Risk Stratification Array data generated from 55 MDS patients and 11 normal controls was analyzed. The patients were sub-classified as follows: refractory anemia (RA) (18 patients), refractory anemia with ring sideroblasts (RARS) (19 patients), refractory anemia with excess blasts (RAEB): RAEB-1 and RAEB-2 (18 patients).

Figure 1B:
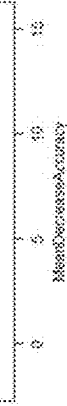
FIG. 1B depicts a 2D scatter plot showed a significantly ($p=0.0007$) negative correlation (Pearson $r=-0.4068$) between the GPI anchor biosynthesis gene panel and the CIN70 signature by plotting the first principal component (PC1) of each individual per gene panel.
Figure 1C:
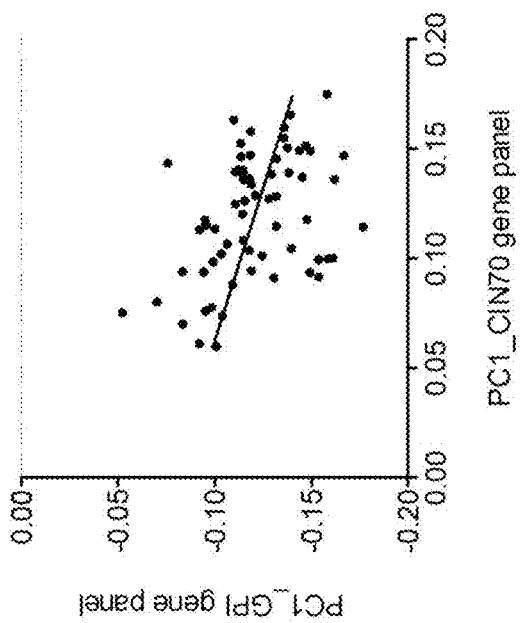
FIG. 1C depicts results showing that PIGN was ranked third among GPI-AP biosynthesis genes in predicting MDS risk stratification based on a Random Forest classifier using Mean Decrease in Accuracy as predictor.

Overall, CIN70 genes were expressed in a MDS disease subtype-dependent manner with a relatively lower expression in high-risk disease subtypes (REAB-1 and RAEB-2) compared to the low risk subtypes (RA and RARS) and normal controls. This heat map showed that the expression of the CIN-70 gene panel was associated with MDS risk stratification (FIG. 1A). A randomForest analysis further demonstrated a significant (p=0.0007) correlation (Pearson r=−0.4068) between GPI-anchor biosynthesis gene panel and the CIN-70 genomic instability marker panel (FIG. 1B). Furthermore, the mean decrease in accuracy identified PIGN gene as highly important (i.e. 3rd ranked) among the GPI-AP biosynthesis genes in predicting MDS progression risk (FIG. 1C).

Figures 2A, 2B:
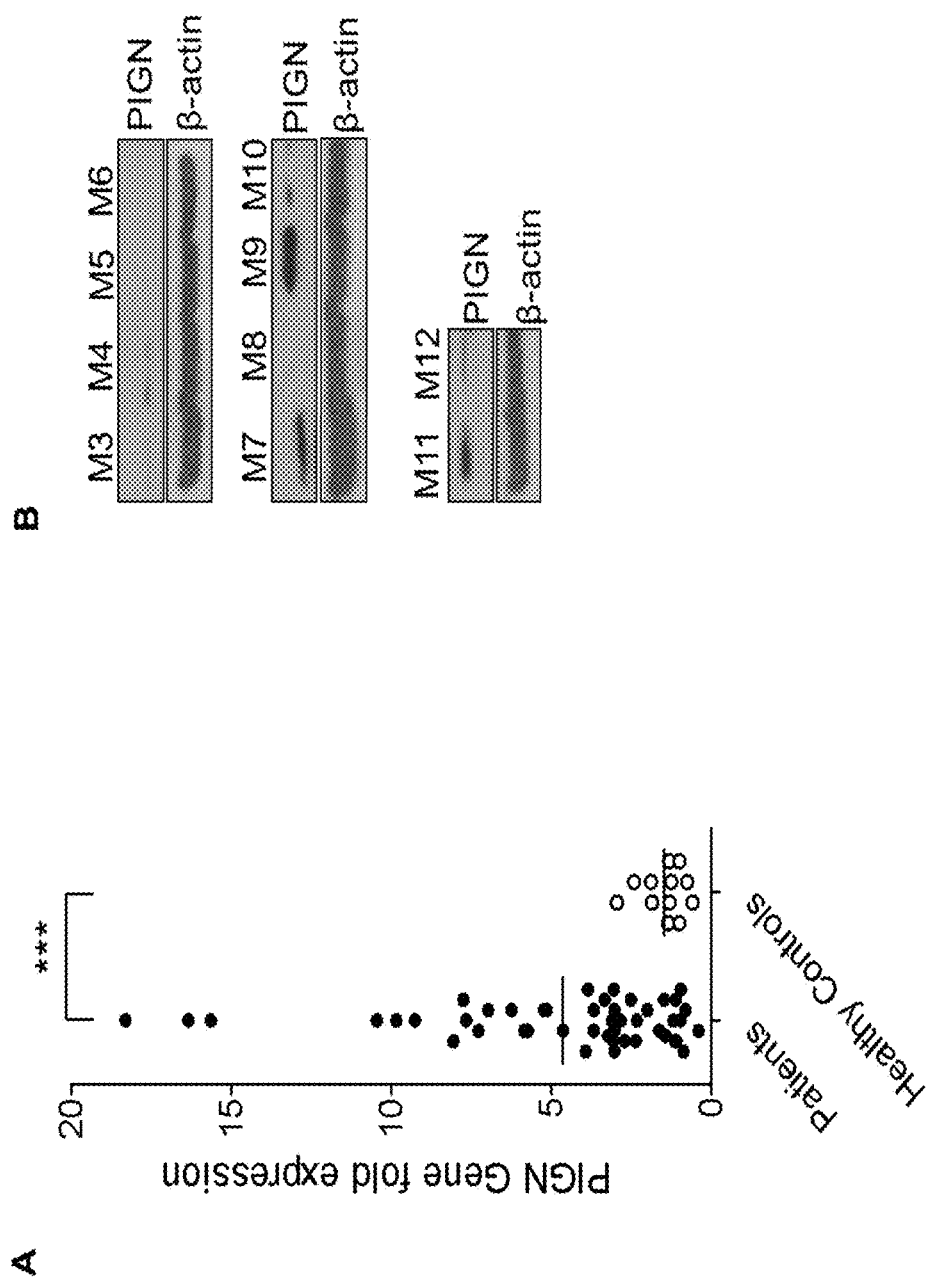
FIG. 2A through FIG. 2C, depicts experimental results demonstrating that PIGN gene expression aberration was due to truncation.

PIGN Gene Expression Aberrations Occur in a Subgroup of Patients with MDS or AML-MRC RT-qPCR was used to determine the PIGN gene expression profiles of CD34+ mononuclear cells harvested from the peripheral blood or bone marrow aspiration of 48 patient samples with either high risk MDS or AML-MRC and 12 healthy volunteers. The results revealed that, majority (~60%) of these patients had a significantly (p<0.0001) higher expression of the PIGN gene in comparison with the cells from healthy normal controls (FIG. 2A). Moreover, 15 of 35 patient samples examined for both PIGN transcription and translation had an aberrant expression pattern (i.e. increased transcriptional activity but diminished to no protein production) (Table 1 and FIG. 2B). Overall, these data indicated that, a subgroup of patients with high risk MDS or AML-MRC appeared to have PIGN expression aberration with increased gene expression but diminished protein production.

TABLE 1

PIGN gene and protein expression status in MDS or AML-MRC patients.

| ID | Age/Sex | TP53 Deletion | PIGN Protein Expression | [a]PIGN Gene Fold Expression | Karyotype (Normal/Complex) |
|---|---|---|---|---|---|
| M1 | 60/F | + | − | 3.787 | Complex |
| M2 | 27/F | + | − | 7.653 | Complex |
| M3 | 87/M | − | + | 1.187 | Complex |
| M4* | 59/F | − | + | 3.927 | Complex |
| M5* | 59/F | − | − | 2.703 | Complex |
| M6 | 61/M | − | − | 4.639 | Complex |
| M7 | 78/M | − | + | 1.636 | Complex |
| M8 | 64/M | − | − | 0.398 | Complex |
| M9 | 29/F | − | + | N.D | Complex |
| M10 | 29/F | − | + | 1.435 | Complex |
| M11 | 68/M | − | + | 2.002 | Complex |
| M12 | 61/F | − | + | 3.228 | Normal |
| M13 | 63/F | + | + | 0.873 | Complex |
| M14 | 55/F | − | N.D | 2.323 | Normal |
| M15 | 67/F | − | − | 5.158 | complex |
| M16 | 67/F | − | − | 15.633 | complex |
| M17 | 73/F | − | N.D | 1.150 | Complex |
| M18 | 27/M | − | + | 2.513 | Complex |
| M19 | 48/F | − | − | 7.756 | Complex |
| M20 | 66/F | − | N.D | 3.045 | Complex |
| M21 | 72/F | + | − | 6.974 | Complex |
| M22 | 45/F | − | + | 5.737 | Normal |
| M23 | 46/M | − | − | 3.857 | Complex |
| M24 | 59/M | − | − | 10.461 | Complex |
| M25 | 47/F | − | N.D | 6.246 | Complex |
| M26 | 27/F | + | − | 5.227 | Complex |
| M27 | 37/F | − | N.D | 18.311 | Complex |
| M28 | 56/F | + | − | 9.260 | Complex |
| M29 | 84/F | − | N.D | 3.068 | Complex |
| M30 | 61/M | − | + | 3.328 | Normal |
| M31 | 74/M | + | N.D | 5.849 | Complex |
| M32 | 61/M | − | + | 2.354 | Complex |
| M33 | 74/M | − | N.D | 16.343 | Complex |
| M34 | 74/M | − | N.D | 3.031 | Complex |
| M35 | 65/F | − | N.D | 0.808 | Normal |
| M36 | 65/F | − | + | 0.959 | Normal |
| M37 | 81/F | + | + | 1.490 | Complex |
| M38 | 75/F | − | + | 3.671 | Normal |
| M39 | 85/M | − | N.D | 3.026 | Normal |
| M40 | 71/M | − | + | 3.021 | Complex |
| M41 | 77/M | − | + | 0.962 | Complex |
| M42 | 62/M | − | − | 7.275 | Complex |
| M43 | 49/F | − | − | 9.842 | Complex |
| M44 | 51/F | − | + | 3.676 | Normal |
| M45 | 51/F | − | N.D | 1.096 | Normal |
| M46 | 58/M | + | + | 2.825 | Complex |
| M47 | 68/F | + | + | 1.113 | Complex |
| M48 | 59/M | − | N.D | 8.061 | Complex |

[a]Mean fold difference in gene expression in patients compared to PIGN gene expression in normal healthy control PBMCs.
+: detected
−: not detected
N.D: no data available
*M4 and M5 from the same patient; M4 at pre-treatment phase and M5 at relapse phase.

PIGN Gene Expression Aberrations were Caused by Novel Intronic Retention Mutation Between Exons 14 and 15

Figure 2C:
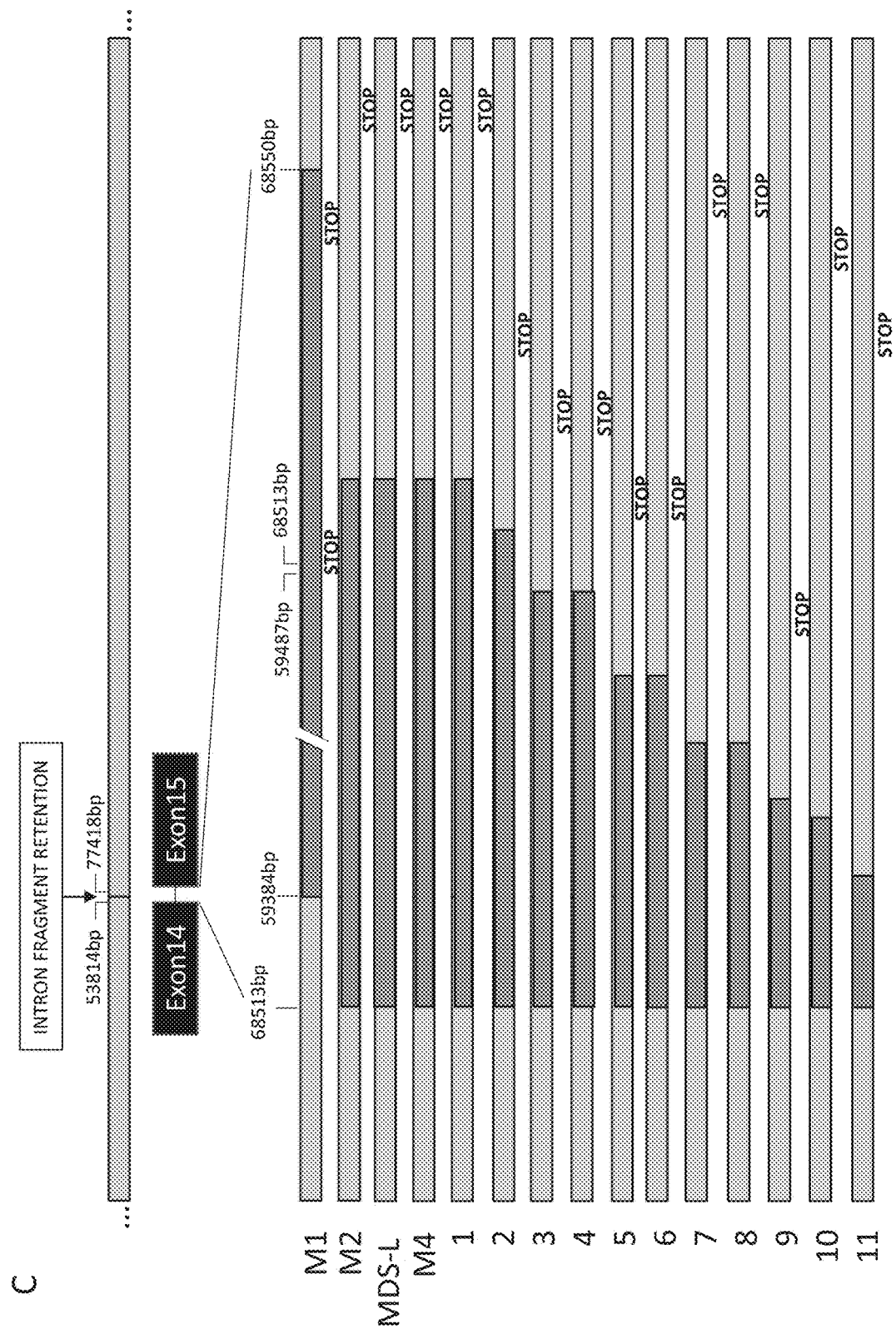

The cause of this PIGN gene expression aberration was explored by cloning and sequencing the PIGN transcripts from 3 patient samples (M1, M2, and M4) and a cell line (MDS-L) which had significantly high PIGN gene expression but no protein expression. Our results revealed the retention of aberrant short intronic fragments (i.e. 11 bp to 142 bp) between exons 14 and 15 (FIG. 2C; 1-4). The predicted product of this mutation is a truncated protein around ~46 kDa which is less than half of the normal protein size (i.e. ~106 kDa). Interestingly, similar variants of this mutation were identified in 11 AML patients from junction files generated from the RNA-seq data of 19 AML patients (dbGaP Study Accession: phs001027.v1.p1) (FIG. 2C; 1-11)

(Trapnell et al., Bioinformatics, 2009, 25:1105-1111). Further examination at the resolution of individual bases of these aberrant transcripts revealed that these intron fragments were similar to those originally identified in the patients with PIGN gene expression aberrations.

Figures 3A, 3B, 3C:
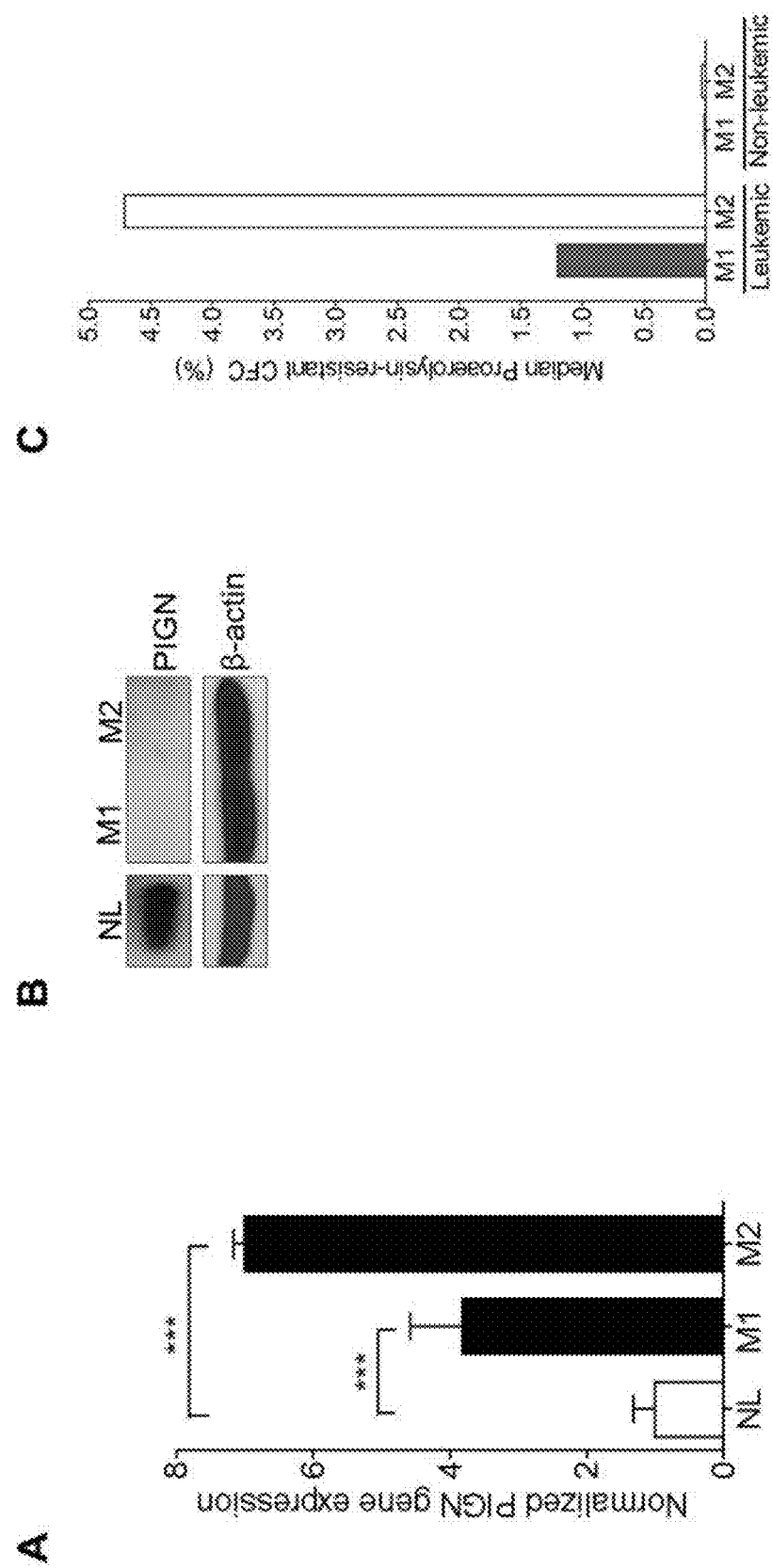
FIG. 3A through FIG. 3C, depicts experimental results demonstrating that PIGN expression aberration resulted in an increased frequency of GPI-AP deficiency.

The Novel Intronic Retention Mutations are Present in Leukemic Cells but not in Non-Leukemic Cells and are Associated with a Relatively High Frequency of GPI-AP Deficiency Using RT-qPCR, PIGN gene expression was examined in sorted leukemic cells from 2 AML patients (M1 and M2). Both patients contained TP53 gene deletion mutations (Table 1). PIGN gene expression in the leukemic cells from these two patients was at least 3-7-fold higher than in the non-leukemic cells (NL); but PIGN protein expression was not detectable in those leukemic cells (FIG. 3A-FIG. 3B). The PIGN transcripts from the sorted leukemic cells and non-leukemic cells were then sub-cloned and sequenced. Interestingly, retention of segments (38 bp and 142 bp) of the intervening intron between exons 14 and 15 was observed in the leukemic cells which resulted in frameshifts and led to the occurrence of premature termination codons (PTCs) (FIG. 2C); but not in the non-leukemic cells.

Elevated frequency of GPI-AP deficiency has been linked with genomic instability and leukemic progression (Chen et al., Cancer Res. 2001, 61:654-658). In order to explore the genetic stability status of those patients, proaerolysin-resistant colony forming cell (CFC) assays were conducted on both sorted leukemic and non-leukemic cells from patients M1 and M2. The GPI-AP deficiency frequency of the two AML patients was calculated as described (Pu et al., Haematologica, 2012, 97:1225-1233). The median frequencies (GPI-AP deficiency frequency) of proaerolysin-resistant leukemic CFC formation for M1 and M2 were 1.20% and 4.71% (ranging from 0.27 to 3.02% and 2.88 to 6.46%) respectively; however, the median frequencies (GPI-AP deficiency frequency) of proaerolysin-resistant non-leukemic CFC formation were 0.009% and 0.029% (ranging from 0.004% to 0.013% and 0.007% to 0.075%) respectively (FIG. 3C). The GPI-AP deficiency frequency in a normal population is approximately 0.002% (Pu et al., Haematologica, 2012, 97:1225-1233). Thus, the GPI-AP deficiency frequencies in the leukemic cells were 100 times higher than in the non-leukemic cells.

Figures 4A, 4B, 4C, 4D, 4E, 4F, 4G:
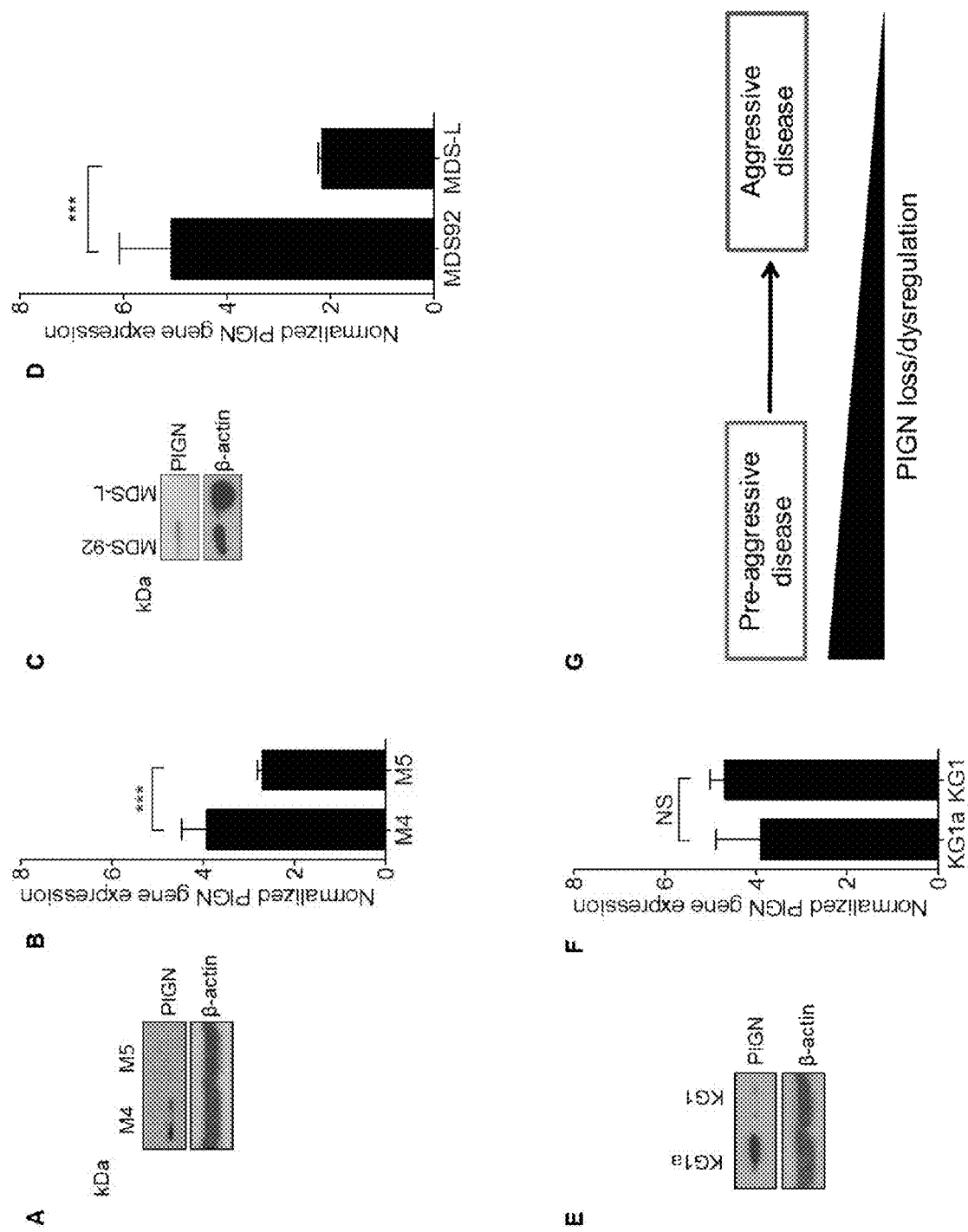
FIG. 4A through FIG. 4G, depicts experimental results demonstrating that PIGN expression aberration is a marker of leukemic transformation and progression.

PIGN Gene Expression Aberrations Occur During Leukemic Transformation and Progression Based on the initial identification of partial intron retentions in the sorted leukemic cells, PIGN gene and protein expression were examined in relation with disease progression in a refractory AML patient (FIG. 4A-FIG. 4B). That patient had 65% leukemic blasts during the pre-treatment phase (M4) and 42% leukemic blasts at the relapse phase (M5). An intron fragment retention was detected between exons 14 and 15 in the pre-treatment mononuclear cells of this patient, similar to those intron fragment retentions earlier identified in the sorted leukemic cells in M1 and M2 (FIG. 2C). However, this intron fragment was not detected in the mononuclear cells collected at the relapse phase. Furthermore, we observed PIGN gene expression aberrations in both phases of disease progression (M4 and M5) in this AML patient, with higher gene expression (~4-fold) in the pre-treatment phase than in the relapse phase (~2.5-fold) compared to normal healthy control cells (FIG. 4A-FIG. 4B), but more suppressed protein expression in the relapse phase.

In order to examine whether PIGN gene expression aberration occurs during leukemic transformation, a cell line model of MDS transformation to AML was employed. This model involves two cell lines (MDS92 and its blastic subline MDS-L) generated from a single patient but with distinct phenotypes representative of the MDS phase and the AML phase of leukemic progression respectively (Tohyama et al., Br J Heamatol. 1994, 87:235-242). PIGN gene and protein expression was examined in these two cell lines. PIGN protein expression was relatively higher in the MDS92 cell line but was not detected in the MDS-L cell line (FIG. 4C). Moreover, a relatively high PIGN gene expression in MDS92 cells (~5.1-fold) and MDS-L cells (~2.2-fold) compared to normal non-leukemic mononuclear cells (FIG. 4D). Thus, PIGN gene expression aberration was more obvious in the leukemic phase than in the MDS phase. Interestingly, the same intron fragment retention was identified in the leukemic phase MDS-L cell line as in leukemic cells from M2 and M4 (FIG. 2C). This mutation was however not detected in the MDS92 cells. Thus, PIGN expression aberration occurs during MDS leukemic transformation and progression and is marked by the presence of partial intron retention mutations between exons 14 and 15, and ultimately the progressive loss of PIGN protein expression. A similar PIGN expression aberration pattern was observed in one (KG1) of two leukemia cell lines (KG1 and KG1a) originated from a single patient, KG1 harboring a myeloblast phenotype and KG1a bearing a stem/progenitor-like phenotype (FIG. 4E-FIG. 4F). However, no intron fragment retention was detected in either cell lines while PIGN gene expression was only marginally different between these two cell lines. Without being bound by a particular theory, the progressive loss of PIGN protein expression in these leukemic cells and cell lines in the different MDS/leukemic progression phases indicated that PIGN loss may mark myeloid leukemia progression from a less aggressive disease state to a more aggressive one (FIG. 4G). However, the partial intron retention mutations between exons 14 and 15 only occur in a subgroup of patients, especially those patients who have not received chemotherapy yet.

Figures 5A, 5B, 5C, 5D, 5E, 5F:
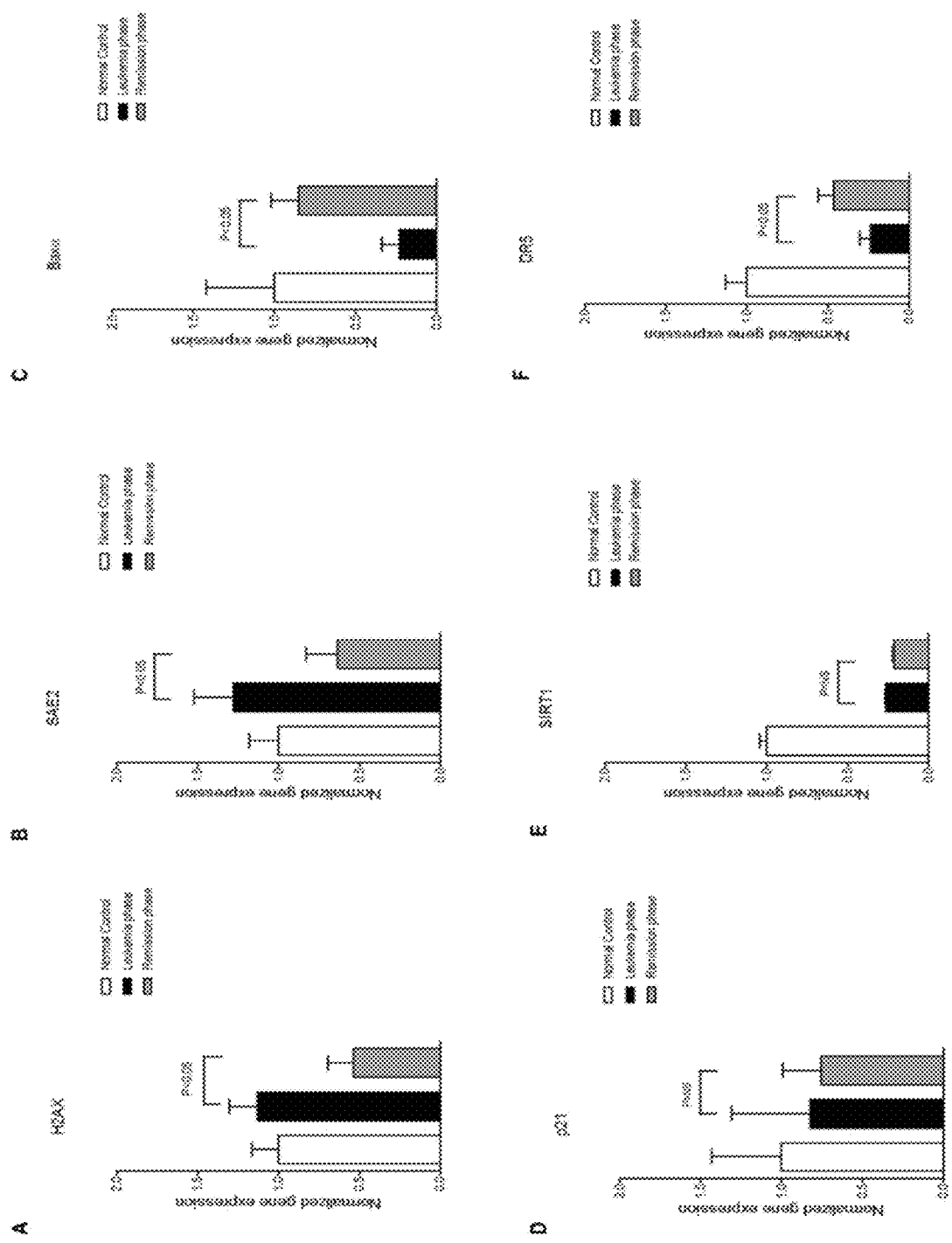
FIG. 5A through FIG. 5F, depicts experimental results demonstrating that PIGN expression aberration was associated with genomic instability in leukemic cells and was TP53-pathway independent.

The Genomic Instability Status in Leukemic Cells was Driven by PIGN Gene Expression Aberration and was TP53 Regulatory Pathway Independent The role of PIGN gene expression aberration in genomic instability was investigated by comparing the gene expression levels of a group of genomic instability/DNA damage related biomarkers in peripheral blood mononuclear cells collected from patient M2 at leukemia active phase and leukemia remission phase. The biomarkers not regulated by TP53 (H2AX and SAE2) manifested a significant transcriptional activation in the leukemia active phase but not in the remission phase (FIG. 5A-FIG. 5B). H2AX is a genomic instability suppressor gene and SAE2 encodes a protein involved in double strand DNA break repair (Turinetto and Giachino, Nucleic Acids Res. 2015, 43:2489-2498; Puddu et al., EMBO J. 2015, 34:1509-1522). BAXα, a pro-apoptotic gene, was significantly downregulated in the leukemia active phase as well (FIG. 5C). However, the expression of TP53 target gene p21 and the TP53 deacetylase gene SIRT1 was not significantly different between leukemia phase and remission phase (FIG. 5D-FIG. 5E). The TP53-dependent TRAIL death receptor DR5 was upregulated in the remission phase but was still about 50% below the DR5 gene expression in the normal control (FIG. 5F).

Figures 8A, 8B, 8C:
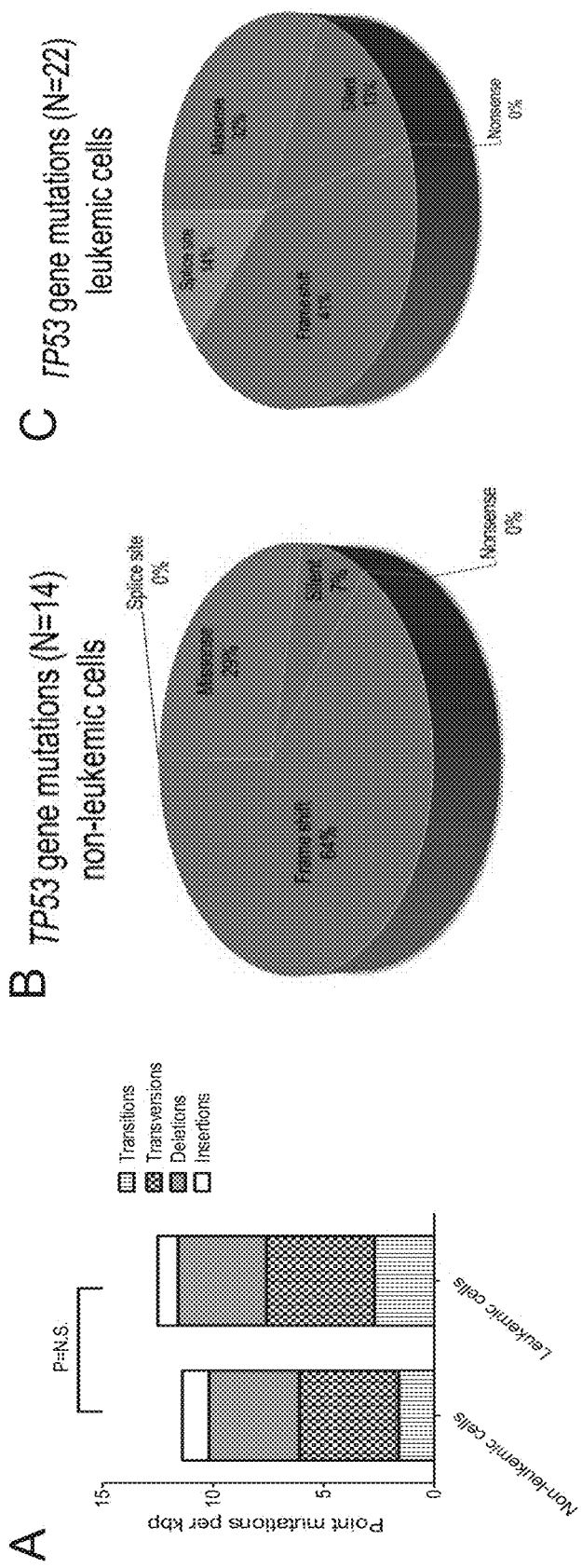
FIG. 8A depicts the combined intron and exon mutation frequency normalized to kilo base pairs (kbp) analyzed of the TP53 gene in non-leukemic and leukemic cells. No statistically significant (P>0.05) differences was found between the groups using students t test.
FIG. 8B depict the qualitative analysis of sequence alteration found in TP53 coding sequences (exons) of non-leukemic cells.
FIG. 8C depicts the same for leukemic cells.

TP53 gene deletion was observed in both M2's leukemic cells and non-leukemic cells. Approximately 2,300 bp of DNA from non-leukemic and leukemic cells spanning exons 2-11 of the TP53 gene was analyzed by Sanger sequencing. However, only three sequence alterations could be verified as a conserved deletion or missense mutations between the different cell types (FIG. 6). There was no significant difference in sequence identity (%) between non-leukemic and leukemic cells derived from patient M2 (FIG. 7A-FIG. 7D). The overall mutation rate was also similar between non-leukemic and leukemic cells with 11.4/kbp and 12.5/kbp respectively (FIG. 8A). Non-leukemic cells displayed in total of 14 sequence alterations in the coding sequence whereas leukemic cells displayed 22 (FIG. 8B-FIG. 8C). However, the PIGN gene expression aberration was only observed in the leukemic cells. Thus, without being bound by a particular theory, it is proposed that PIGN gene expression aberration may be the driving force of high genomic instability in the leukemia cells.

Figures 9A, 9B, 9C, 9D, 9E:
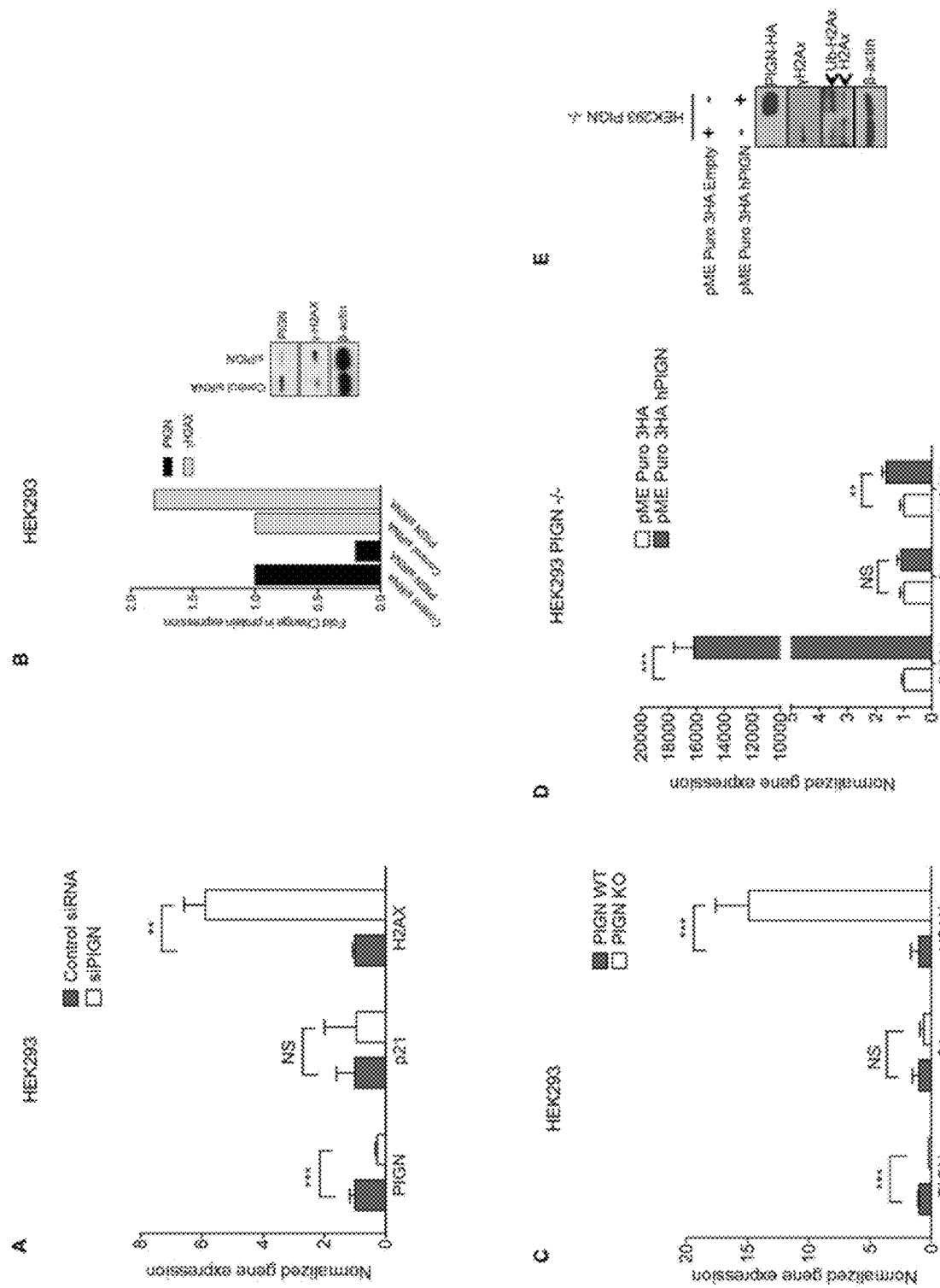
FIG. 9A through FIG. 9J, depicts experimental results demonstrating that PIGN gene expression suppression is associated with genomic instability; and reintroduction of PIGN gene expression restores genomic stability in a TP53-pathway independent manner.
Figures 9F, 9G, 9H, 9I, 9J:
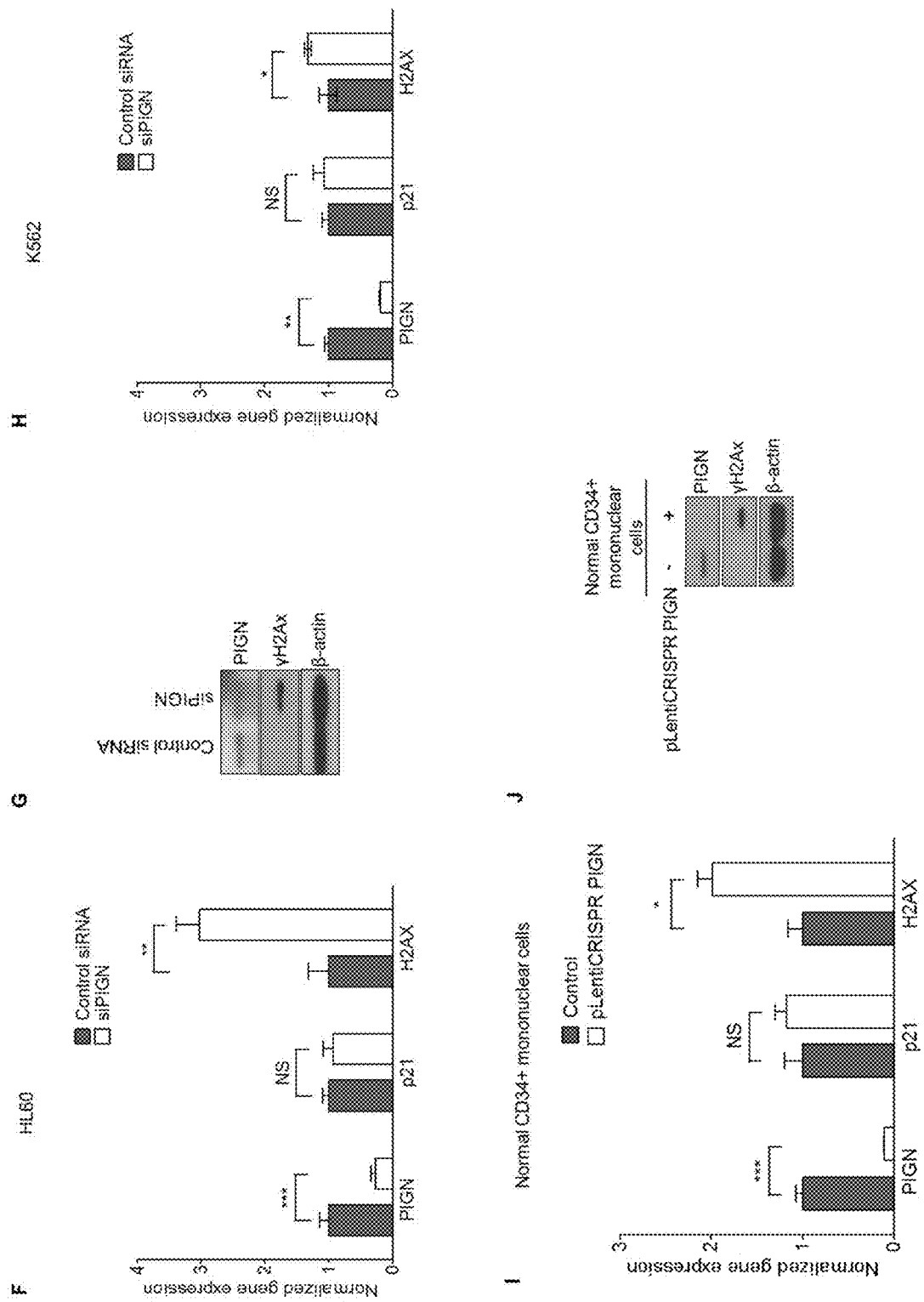

In order to further test the hypothesis that PIGN gene expression aberration can contribute to genomic instability regardless of TP53 gene status, a transient knockdown of PIGN in multiple cell lines with various TP53 gene mutation statuses was employed. The impact of PIGN gene expression suppression or silencing on the gene expression of p21 and H2AX in HL60 (TP53 deletion), K652 (TP53 mutation), HEK293 and HEK293 PIGN KO (TP53 wild type) cell lines and CD34+ mononuclear cells from a healthy individual was investigated. PIGN suppression in HEK293 cells resulted in the upregulation of H2AX transcription and γH2AX induction (FIG. 9A-FIG. 9B). Moreover, CRISPR/Cas9 knockout of PIGN in HEK293 cells confirmed a functional link between PIGN loss and the induction of genomic instability in cells and involved an increased transcription (~15-fold) of H2AX (FIG. 9C). However, genomic instability was reduced as shown by γH2AX downregulation with the restoration of PIGN expression (FIG. 9E). The findings were confirmed in K562 and HL60 cell lines (FIG. 9F-FIG. 9H) and in CD34+ mononuclear cells from a healthy individual (FIG. 9I-FIG. 9J). Interestingly, H2AX expression in these cell lines was not influenced by their TP53 gene mutation status, and p21 gene expression was not influenced by PIGN gene expression status. Thus, PIGN loss or suppression induced genomic instability in a TP53 pathway-independent manner.

PIGN Maintains Genomic Stability, Especially Chromosomal Stability, by Regulating the Mitotic Spindle Assembly Checkpoint Protein MAD1

Figure 10A:
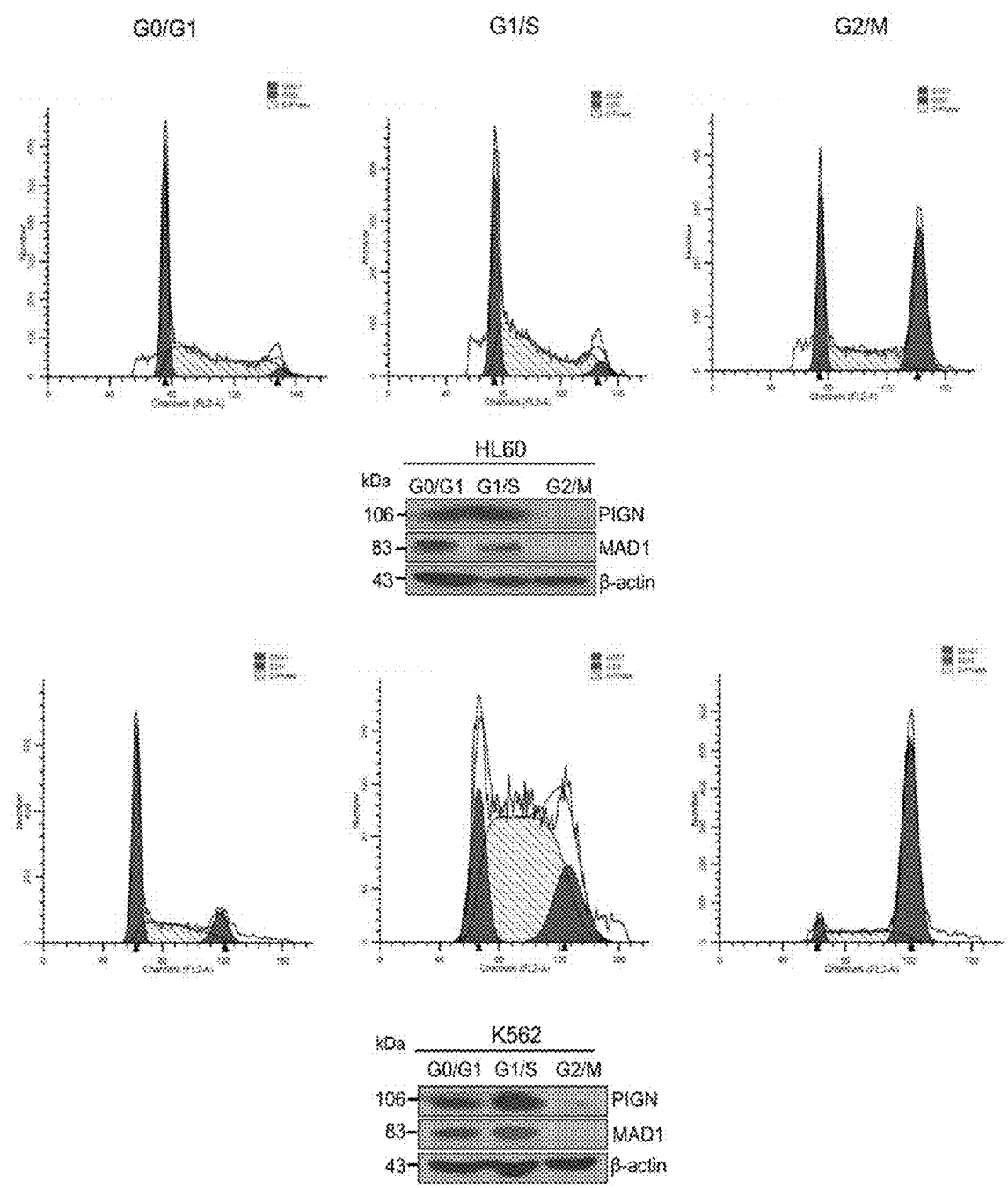
Figures 10H, 10I:
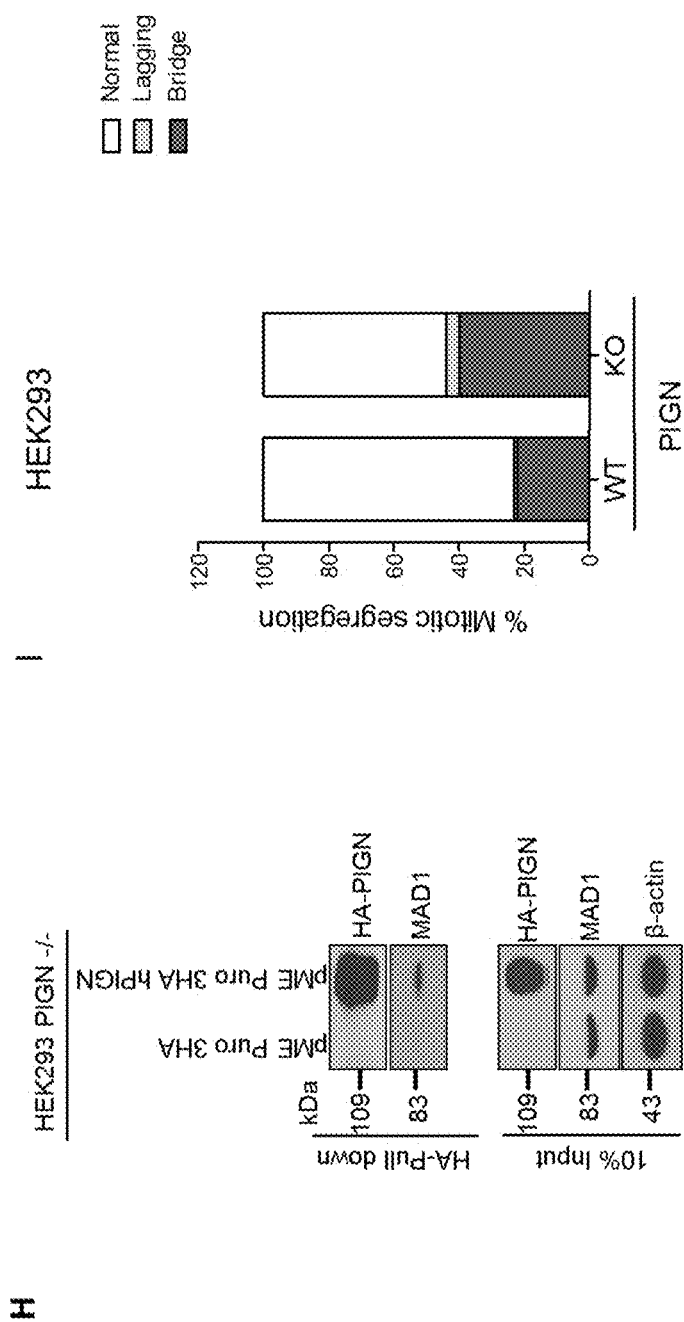
Figure 10J:
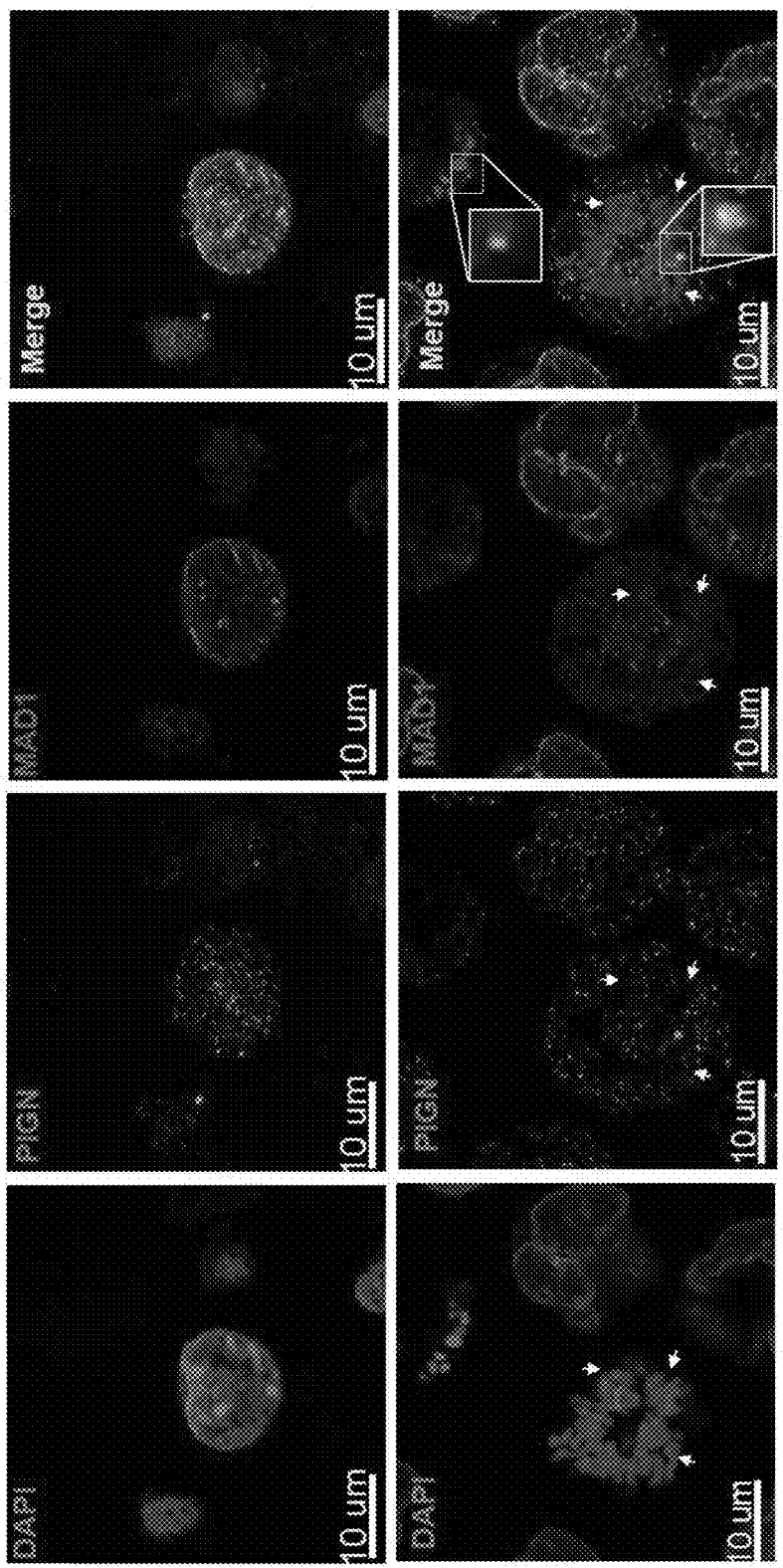
Figure 10K:
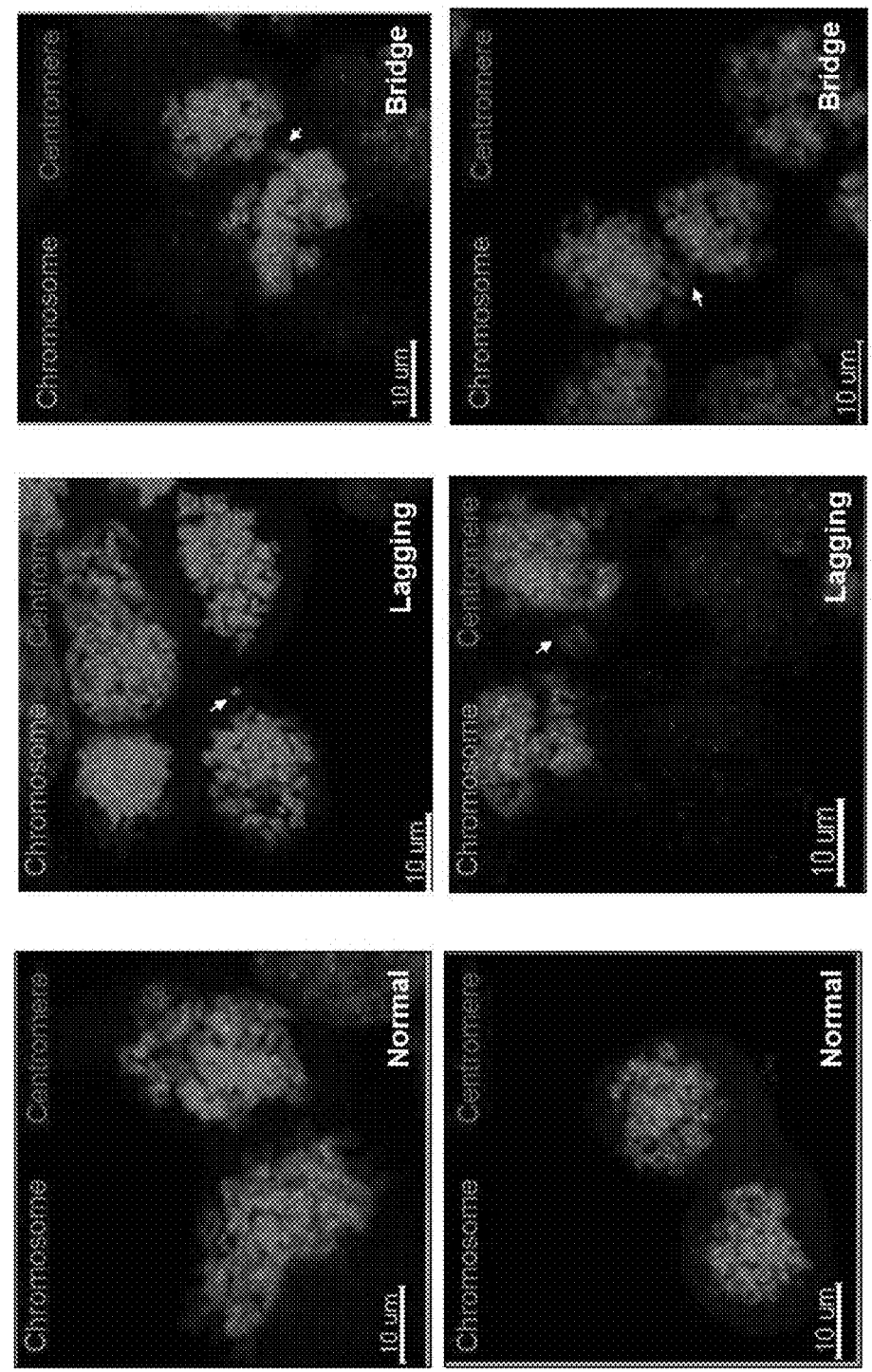

The mechanistic role of PIGN in maintaining genomic stability was further investigated. Cell cycle experiments were conducted by blocking cell cycle progression at G0/G1, S and G2/M phases in HL60 and K562 cells via serum starvation, double-thymidine and nocodazole treatment respectively. A cell-cycle dependent expression of PIGN was observed which correlated with the expression of the spindle assembly checkpoint (SAC) protein MAD1. PIGN and MAD1 were least expressed in the G2/M phase of the cell cycle (FIG. 10A). The SAC is primarily responsible for ensuring proper chromosomal segregation during metaphase-anaphase transition (Musacchio and Salmon, Nat. Rev. Mol. Cell Biol. 2007, 8:379-393). PIGN suppression/knockout caused MAD1 expression suppression, even in CD34+ mononuclear cells derived from a healthy individual (FIG. 10B-FIG. 10F). Alternatively, MAD1 suppression resulted in decreased expression of PIGN (FIG. 10G). These findings revealed a novel reciprocal regulation between the SAC component MAD1 and PIGN. To further investigate the relationship between PIGN and MAD1, CRISPR/Cas9 PIGN KO HEK293 cells were transfected with an HA-tagged PIGN and a HA-tag pulldown assay was performed. A direct interaction between PIGN and MAD1 was observed, with the highest interaction at 48 hours post-transfection (FIG. 10H). Confocal analyses also revealed co-localization of MAD1 and PIGN during prometaphase in K562 cells (FIG. 10J). PIGN loss was also accompanied by an increase in the frequency of missegregation errors in PIGN CRISPR/Cas9 knockout HEK293 cells (FIG. 10I and FIG. 10K). The same experiments were conducted on a leukemia patient sample (M4), HL60 and K562 cells with similar observations (data not shown). The above data indicated that PIGN maintains chromosomal stability by interaction with the SAC protein MAD1 during the cell cycle.

Genomic instability is a driving force for cancer initiation and progression. Previous studies have indicated that cell lines with genomic instability (i.e. Fanconi anemia and colon cancer cells with a mutator phenotype) had a marked increase in frequency of acquiring GPI-AP deficiency (Araten et al., Mutat. Res.-Fundam. Mol. Mech. Mutagen. 2010, 686:1-8; Araten et al., Cancer Res. 2005, 65:8111-8117; Peruzzi et al., Mutat. Res.-Rev. Mutat. Res. 2010, 705:3-10). It has also been shown that MDS and myeloproliferative diseases (MPD) patients bearing high frequency of GPI-AP deficiency posed a higher risk for leukemic transformation (Pu et al., Haematologica, 2012, 97:1225-1233). Using bioinformatics tools to screen existing databases a negative correlation between GPI-AP biosynthesis genes and genomic instability has been identified, in which the PIGN gene was highly ranked as a predictor of MDS progression risk (Pellagatti et al., Blood, 2006, 108:337-345). PIGN gene expression profiles showed a unique gene expression aberration pattern within a subgroup of patients with MDS or AML-MRC. PIGN protein loss was linked to the presence of fragment retentions of the intervening intron between exons 14 and 15 that caused frameshifts and early translational termination. This intron retention mutation was also identified in multiple AML patients based on RNA-seq data analyses (phs001027.v1.p1) that verified the conserved nature of this mutation. However, no such natural alternative splice variants of PIGN gene have been reported (Ensembl release 85: ENSG00000197563). Thus, the novel intron fragment retention identified herein is not a natural alternative splice variant. Similar deleterious splice defects have previously been reported for other genes including DMD, C9orf72 and GR associated with muscular dystrophy, amyotrophic lateral sclerosis/frontotemporal dementia (ALS/FTD) and small cell lung cancer respectively (Gonorazky et al., Ann. Clin. Transl. Neurol. 2016, 3:55-60; Niblock et al., Acta Neuropathol. Commun. 2016, 4:18; Parks et al., Mol. Cell. Endocrinol. 1998, 142:175-181). Moreover, splicing factor genes have been reported to be mutated in MDS and AML (Ogawa, Int. J. Hematol. 2012, 96:438-442).

PIGN gene expression aberration and partial intron retention was also identified in a pre-treatment sample (M4) from an AML patient. Despite progressive loss of PIGN protein expression continued in the relapse sample (M5), this intron fragment retention was not detected. Without being bound by a particular theory, it is believed that this may be treatment related, because chemotherapy could have cleared that initial leukemic subclone bearing the intron retention mutations but the chemo-resistant clones survived and proliferated, which could explain why PIGN protein expression was not observed in M5. Earlier studies have demonstrated the occurrence of multiple clones with varied sensitivity to chemotherapy (Stiehl et al., J R Soc Interface. 2014, 11:20140079; Cogle et al., Cancer Letters, 2016, 552-560).

The data from patient samples, cell lines and existing databases are in line with previous observations that elevated frequency of GPI-AP deficiency is a marker of genomic instability and might predict a risk of leukemic transformation and progression (Chen et al., Cancer Res. 2001, 61:654-658; Araten et al., Cancer Res. 2005, 65:8111-8117; Peruzzi et al., Mutat. Res.-Rev. Mutat. Res. 2010, 705:3-10). Furthermore, this study indicated that PIGN gene expression aberration may be the key factor linking GPI-AP deficiency with CIN and leukemogenesis. Previous studies demonstrated that, unlike PIGA, PIGN gene loss would not completely eliminate GPI-AP biosynthesis (Hong et al., J. Biol. Chem. 1999, 274:35099-35106; Ohba et al., Neurogenetics. 2014, 15:85-92). Without being bound by a particular theory, this piece of data may explain why the leukemic cells from patients M1 and M2 still showed sign of CFC formation reduction in proaerolysin-containing medium though the CFC counts were significantly higher than the normal control.

The role of PIGN gene expression aberration in genomic instability/leukemic progression and the role of the TP53 signaling pathway in the regulation of genomic instability during leukemia progression was investigated by studying the leukemic cells from patient M2, and several cell lines. In this patient, TP53 gene deletion was observed in both leukemic cells and non-leukemic cells and manifested with a similar mutation profile, however, the PIGN gene expression aberration only occurred in the leukemic cells. The gene expression of TP53-independent genomic instability/DNA damage markers (H2AX and SAE2) were upregulated and the expression of the pro-apoptosis marker BAXα was downregulated specifically in the leukemic cell-rich mononuclear cells at the active leukemia phase when compared to the cells from the remission phase. However, the expressions of TP53-dependent biomarkers, such as p21 and SIRT1, were not significantly different between the active phase and the remission phase. Furthermore, the expression of the TRAIL death receptor 5 (DR5) was below 50% of that of the normal control in both active phase and the remission phase. Suppression or elimination of PIGN gene expression in several cell lines and CD34+ mononuclear cells from healthy individuals induced a similar TP53 independent pattern of genomic instability which could be reversed via PIGN gene expression restoration (FIG. 9A-FIG. 9J).

The data demonstrated that PIGN gene expression aberration was associated with genomic instability in leukemia cells and was independent of the TP53 regulatory pathway. A similar phenomenon was reported in normal epithelium of benign breast tissue within the same breast cancer patients (Kandel et al., Int. J. Cancer. 2000, 87:73-780. Wong et al. earlier also reported the presence of functional TP53 mutations in mononuclear cells isolated from healthy individuals (Wong et al., Nature. 2015, 518:552-555). It was suggested that TP53 loss may be permissive rather than causative with regards to genomic instability (Burrell et al., Nature 2013, 494:492-496; Bunz et al., Cancer Res. 2002, 62:1129-1133). Thus, this is likely a reflection of the loss of the CIN suppressor PIGN, facilitating TP53 gene loss of heterozygosity (LOH) in leukemic cells and corroborates the fact that TP53 loss alone is insufficient for the promotion of genomic instability in those cells (Burrell et al., Nature 2013, 494: 492-496; Bunz et al., Cancer Res. 2002, 62:1129-1133; Hermsen et al., PLoS One. 2015, 10:e0122066). The findings herein are also consistent with previous observations on Li-Fraumeni Syndrome (LFS) patients and may explain why those patients are prone to develop therapy-related MDS with complex cytogenetics and poor prognosis (Talwalkar et al., Arch. Pathol. Lab. Med. 2010, 134:1010-1015).

PIGN protein was historically known as a membrane protein involved in GPI-AP biosynthesis, however, PIGN directly interacts with the SAC protein MAD1. PIGN loss resulted in the dysregulation of MAD1 during cell cycle progression and was associated with an increased frequency of mitotic missegregation. PIGN and MAD1 were expressed similarly in a cell cycle-dependent manner with a subtle co-localization during prometaphase and the least expression in the mitotic phase relative to the G0/G1 and S phases. Without being bound by a particular theory, this decline in expression at mitotic block may be the natural process for microtubule/spindle detachment from the kinetochore or could be due the spindle disrupting effect of nocodazole treatment which may in turn result in the destabilization and degradation of the MAD1-PIGN complex. This study showed for the first time that PIGN could directly interact with SAC protein complex at the mitotic phase of cell cycle to regulate chromosome stability. Thus, without being bound by a particular theory, a novel model of PIGN regulation of chromosome stability via interaction and regulation of the SAC protein MAD1 is postulated.

Recent literature has shown an association between increased expression of the interferon-inducible double-stranded RNA-activated protein kinase (PKR, also referred to as EIF2AK2) and both decreased expression of genomic instability biomarkers and increased incidence of leukemia-related somatic mutations in AML patients, cell lines, and mouse model (Cheng et al., Blood. 2015, 126:1585-1594). Therefore, PKR is another potential interacting partner of PIGN during the cell cycle.

In conclusion, PIGN is a novel biomarker of CIN and leukemic transformation/progression in a subgroup of patients with MDS or AML-MRC. This study provides additional evidence for the necessity of updating our MDS/AML risk estimation stratification system, and may help to develop novel MDS/AML therapy specifically targeting CIN.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of detecting a mutation in PIGN comprising:
obtaining a blood or bone marrow sample from a subject;
isolating mononuclear cells from the sample;
determining a PIGN transcription level in the mononuclear cells;
determining a PIGN translation level in the mononuclear cells;
comparing the PIGN transcription level to the PIGN translation level;
determining whether there is an increase in the PIGN transcription level and a decrease in the PIGN translation level; and
sequencing the PIGN gene to locate a mutation.

2. The method of claim 1, wherein the mononuclear cells comprise lymphocytes, monocytes, or combinations thereof.

3. The method of claim 1, wherein the step of determining the PIGN transcription level comprises a Northern blot, qPCR, RT-PCR, RT-qPCR, an amplification-based method, a signal amplification method, a nuclease protection assay, in situ hybridization, or combinations thereof.

4. The method of claim 1, wherein the step of determining the PIGN translation level comprises an enzyme assay, an immunoassay, mass spectrometry, chromatography, electrophoresis, an antibody microarray, or combinations thereof.

5. The method of claim 1, wherein the step of sequencing the PIGN gene comprises Sanger sequencing and PCR-based sequencing.

* * * * *